(12) United States Patent
Mattson et al.

(10) Patent No.: US 6,642,232 B2
(45) Date of Patent: Nov. 4, 2003

(54) 3-[4-SUBSTITUTED HETEROCYCLYL)-PYRROL-2-YLMETHYLIDENE]-2-INDOLINONE DERIVATIVES AS KINASE INHIBITORS

(75) Inventors: Matthew Mattson, Santa Clara, CA (US); Tomas Vojkovsky, San Mateo, CA (US); Congxin Liang, Sunnyvale, CA (US); Peng Cho Tang, Morago, CA (US); Huiping Guan, Foster City, CA (US)

(73) Assignee: Sugen, Inc., South San Francisco, CA (US)

( * ) Notice: Subject to any disclaimer, the term of this patent is extended or adjusted under 35 U.S.C. 154(b) by 0 days.

(21) Appl. No.: 10/268,082

(22) Filed: Oct. 10, 2002

(65) Prior Publication Data

US 2003/0130235 A1 Jul. 10, 2003

Related U.S. Application Data

(60) Provisional application No. 60/328,226, filed on Oct. 10, 2001.

(51) Int. Cl.$^7$ .................. A61K 31/5377; A61P 35/00; C07D 413/14
(52) U.S. Cl. ................. 514/235.2; 544/130; 544/144; 544/121; 546/193; 546/201; 548/468
(58) Field of Search ................. 544/130, 144; 548/468; 514/235.2

(56) References Cited

U.S. PATENT DOCUMENTS

| | | |
|---|---|---|
| 2,622,980 A | 12/1952 | Copeland |
| 2,872,372 A | 2/1959 | Hull |
| 2,968,557 A | 1/1961 | Burgandt et al. |
| 3,140,180 A | 7/1964 | Fritz |
| 3,308,134 A | 3/1967 | Plostneiks |
| 3,551,571 A | 12/1970 | Pachter et al. |
| 3,564,016 A | 2/1971 | Schoen et al. |
| 3,715,364 A | 2/1973 | Hoff |
| 3,880,871 A | 4/1975 | Haugwitz et al. |
| 3,922,163 A | 11/1975 | Church et al. |
| 4,002,643 A | 1/1977 | Carson |
| 4,002,749 A | 1/1977 | Rovnyak |
| 4,053,613 A | 10/1977 | Rovnyak et al. |
| 4,070,366 A | 1/1978 | Gregorovich et al. |
| 4,259,345 A | 3/1981 | Cross et al. |
| 4,259,346 A | 3/1981 | Stähle et al. |
| 4,343,923 A | 8/1982 | Lenox et al. |
| 4,376,110 A | 3/1983 | David et al. |
| 4,436,892 A | 3/1984 | Zondler et al. |
| 4,489,089 A | 12/1984 | Wright, Jr. et al. |
| 4,493,842 A | 1/1985 | Furazawa et al. |
| 4,560,700 A | 12/1985 | Schnettler et al. |
| 4,628,105 A | 12/1986 | Schmid et al. |
| 4,642,309 A | 2/1987 | Michel et al. |
| 4,678,798 A | 7/1987 | Rentzea et al. |
| 4,826,847 A | 5/1989 | Michel et al. |
| 4,853,403 A | 8/1989 | Shiraishi et al. |
| 4,853,404 A | 8/1989 | Takamura et al. |
| 4,868,304 A | 9/1989 | Larock |
| 4,924,000 A | 5/1990 | Hesse et al. |
| 4,966,849 A | 10/1990 | Vallee et al. |
| 4,971,996 A | 11/1990 | Shiraishi et al. |
| 4,987,146 A | 1/1991 | Rohde et al. |
| 5,043,348 A | 8/1991 | Zoller et al. |
| 5,043,454 A | 8/1991 | Wriede et al. |
| 5,047,554 A | 9/1991 | Ehrgott et al. |
| 5,051,417 A | 9/1991 | Nadler et al. |
| 5,057,538 A | 10/1991 | Shiraishi et al. |
| 5,082,856 A | 1/1992 | Taniguchi et al. |
| 5,089,516 A | 2/1992 | Shiraishi et al. |
| 5,124,347 A | 6/1992 | Connor et al. |
| 5,145,983 A | 9/1992 | West |
| 5,153,217 A | 10/1992 | Taniguchi et al. |
| 5,196,446 A | 3/1993 | Levitzki et al. |
| 5,202,341 A | 4/1993 | Shiraishi et al. |
| 5,206,261 A | 4/1993 | Kawaguchi et al. |
| 5,217,999 A | 6/1993 | Levitzki et al. |
| 5,258,357 A | 11/1993 | Muenster et al. |
| 5,278,184 A | 1/1994 | Artico et al. |
| 5,290,947 A | 3/1994 | Zoller et al. |
| 5,302,606 A | 4/1994 | Spada et al. |
| 5,322,950 A | 6/1994 | Sircar et al. |
| 5,330,992 A | 7/1994 | Eissenstat et al. |
| 5,332,736 A | 7/1994 | Carmosin et al. |
| 5,374,652 A | 12/1994 | Buzzetti et al. |
| 5,382,593 A | 1/1995 | Le Baut et al. |

(List continued on next page.)

FOREIGN PATENT DOCUMENTS

| | | |
|---|---|---|
| AU | 286870 | 5/1967 |
| CA | 2012634 A1 | 9/1991 |
| DE | 878539 | 6/1953 |

(List continued on next page.)

OTHER PUBLICATIONS

Abramovitch and Hey, "Internuclear cyclisation. Part VIII. Naphth[3:2:1–cd]oxindoles," *J. Chem. Soc.* 1697–1703 (1954), Strand, London.

Abramovitch et al., "A Novel Synthesis of a Cyclic Hydroxamic Acid Involving a Molecular Rearrangement," *Chemistry and Industry* 44:1871 (1967) ©Laporte Industries Limited, Lancashire.

Beilstein Reg. No. 236050, Beilstein Reference No. 4–21–00–06355.

(List continued on next page.)

*Primary Examiner*—Robert W. Ramsuer
(74) *Attorney, Agent, or Firm*—Beth A. Burrous; Foley & Lardner

(57) ABSTRACT

The present invention relates to certain 3-[4-(substituted heterocyclyl)-pyrrol-2-ylmethylidene]-2-indolinone derivatives that inhibit kinases, in particular VEGFR and/or PDGFR kinases. Pharmaceutical compositions comprising these compounds, methods of treating diseases mediated by kinases utilizing pharmaceutical compositions comprising these compounds, and methods of preparing them are also disclosed.

25 Claims, No Drawings

U.S. PATENT DOCUMENTS

| | | | |
|---|---|---|---|
| 5,389,661 A | 2/1995 | Sircar et al. |
| 5,397,787 A | 3/1995 | Buzzetti et al. |
| 5,409,930 A | 4/1995 | Spada et al. |
| 5,409,949 A | 4/1995 | Buzzetti et al. |
| 5,463,052 A | 10/1995 | Haga et al. |
| RE35,096 E | 11/1995 | Taniguchi et al. |
| 5,565,324 A | 10/1996 | Still et al. |
| 5,610,173 A | 3/1997 | Schwartz et al. |
| 5,723,665 A | 3/1998 | Kato et al. |
| 5,786,488 A | 7/1998 | Tang et al. |
| 5,792,783 A | 8/1998 | Tang et al. |
| 5,834,504 A | 11/1998 | Tang et al. |
| 5,849,710 A | 12/1998 | Battistini et al. |
| 5,880,141 A | 3/1999 | Tang et al. |
| 5,883,113 A | 3/1999 | Tang et al. |
| 5,883,116 A | 3/1999 | Tang et al. |
| 5,886,020 A | 3/1999 | Tang et al. |
| RE36,256 E | 7/1999 | Spada et al. |
| 6,130,239 A | 10/2000 | Chen et al. |
| 6,133,305 A | 10/2000 | Tang et al. |
| 6,248,894 B1 | 6/2001 | Phillion et al. |
| 6,310,217 B1 | 10/2001 | Lehr |
| 6,395,736 B1 | 5/2002 | Parks et al. |
| 6,451,838 B1 | 9/2002 | Moon et al. |
| 6,462,048 B2 | 10/2002 | Howard |
| 6,462,072 B1 | 10/2002 | Hamilton et al. |

FOREIGN PATENT DOCUMENTS

| | | | |
|---|---|---|---|
| DE | 2159360 A | 6/1973 |
| DE | 2159361 A | 6/1973 |
| DE | 2159362 | 6/1973 |
| DE | 2159363 A | 6/1973 |
| DE | 2321656 A | 11/1973 |
| DE | 3426419 A | 1/1986 |
| EP | 0 252 713 B1 | 1/1988 |
| EP | 0 304 493 B1 | 3/1989 |
| EP | 0 351 213 A2 | 1/1990 |
| EP | 0 525 472 A2 | 2/1993 |
| EP | 0 566 226 B1 | 10/1993 |
| EP | 0 580 502 B1 | 1/1994 |
| EP | 0 626 377 B1 | 11/1994 |
| EP | 0 632 102 A1 | 1/1995 |
| EP | 0 662 473 A1 | 7/1995 |
| EP | 0 769 947 B1 | 5/1997 |
| EP | 0 788 890 A1 | 8/1997 |
| EP | 0 810 217 A1 | 12/1997 |
| EP | 0 934 931 A2 | 8/1999 |
| EP | 1 082 305 A1 | 3/2001 |
| FR | 1.398.224 | 5/1965 |
| FR | 1.599.772 | 8/1970 |
| FR | 2.689.397 A1 | 10/1993 |
| GB | 809691 | 3/1959 |
| GB | 835473 | 5/1960 |
| JP | 62-29570 A | 2/1987 |
| JP | 62-39564 A | 2/1987 |
| JP | 63-141955 A | 6/1988 |
| JP | 5-58894 A | 3/1993 |
| WO | WO 88/07035 A1 | 9/1988 |
| WO | WO 91/13055 A2 | 9/1991 |
| WO | WO 91/15495 A1 | 10/1991 |
| WO | WO 92/03736 A1 | 3/1992 |
| WO | WO 92/07830 A2 | 5/1992 |
| WO | WO 92/20642 A1 | 11/1992 |
| WO | WO 92/21660 A1 | 12/1992 |
| WO | WO 93/01182 A1 | 1/1993 |
| WO | WO 93/23040 A1 | 11/1993 |
| WO | WO 94/03427 A1 | 2/1994 |
| WO | WO 94/10202 A1 | 5/1994 |
| WO | WO 94/14808 A1 | 7/1994 |
| WO | WO 95/01349 A1 | 1/1995 |
| WO | WO 95/14667 A1 | 6/1995 |
| WO | WO 95/17181 A1 | 6/1995 |
| WO | WO 95/24190 A2 | 9/1995 |
| WO | WO 96/00226 A1 | 1/1996 |
| WO | WO 96/16964 A1 | 6/1996 |
| WO | WO 96/22976 A1 | 8/1996 |
| WO | WO 96/32380 A1 | 10/1996 |
| WO | WO 96/40116 A1 | 12/1996 |
| WO | WO 97/25986 A1 | 7/1997 |
| WO | WO 97/34920 A1 | 9/1997 |
| WO | WO 97/36867 A1 | 10/1997 |
| WO | WO 98/07695 A1 | 2/1998 |
| WO | WO 98/07835 A2 | 2/1998 |
| WO | WO 98/24432 A2 | 6/1998 |
| WO | WO 98/38984 A2 | 9/1998 |
| WO | WO 98/45708 A1 | 10/1998 |
| WO | WO 98/50356 A1 | 11/1998 |
| WO | WO 98/56376 A1 | 12/1998 |
| WO | WO 99/10325 A1 | 3/1999 |
| WO | WO 99/19325 A1 | 4/1999 |
| WO | WO 99/48868 A2 | 9/1999 |
| WO | WO 99/52869 A1 | 10/1999 |
| WO | WO 99/61422 A1 | 12/1999 |
| WO | WO 99/65869 A1 | 12/1999 |
| WO | WO. 00/08202 A2 | 2/2000 |
| WO | WO 00/35908 A1 | 6/2000 |
| WO | WO 00/38519 A1 | 7/2000 |
| WO | WO 00/56709 A1 | 9/2000 |
| WO | WO 01/37820 A2 | 5/2001 |
| WO | WO 01/60814 A2 | 8/2001 |
| WO | WO 02/055517 A2 | 7/2002 |

OTHER PUBLICATIONS

Akbasak and Sunar–Akbasak, "Oncogenes: cause or consequence in the development of glial tumors," *J. Neurol Sci.* 111:119–133 (1992)© Elsevier Science Publishers.

Andreani et al., "Potential Antitumor Agents. 25[1]. Synthesis and Cytotoxic Activity of 3–(2–Chloro– 3–Indolymethylene)1,3–Dihydroindol–2–Ones," *Anticancer Research* 16:3585–3588 (1996) © Elsevier, Paris.

Andreani et al., "Synthesis and cardiotonic activity of 2–indolinones," *Eur. J. Med. Chem.* 25:187–190 (1990).

Andreani et al., "Synthesis and cardiotonic activity of 2–indolinones bearing pyridyl groups," *Eur. J. Med. Chem.* 28:653–657 (1993) © Elsevier, Paris.

Andreani et al., "Synthesis and cardiotonic activity of 2–indolinones," *Chemical Abstracts,* vol. 113, abstract No. 78106 (1990).

Andreani et al., "Synthesis and cardiotonic activity of pyridylmethylene–2–indolinones," *Eur. J. Med. Chem.* 27:167–170 (1992) © Elsevier, Paris.

Andreani et al., "Synthesis and potential coanthracyclinic activity of substituted 3–(5–imidazo[2,1–b]thiazolylmethylene)–2–indolinones," *Eur. J. Med. Chem.* 32:919–924 (1997) © Elsevier, Paris.

Andreani et al., "Synthesis of lactams with potential cardiotonic activity," *Eur. J. Med. Chem.* 28:825–829 (1993).

Andreani et al., "In Vivo Cardiotonic Activity of Pyridylmethylene–2–indolinones," *Arzneimittle–Forschung Drug Research* 48:727–729 (1998) ©.

Arteaga et al., "Blockade of the Type I Somatomedin Receptor Inhibits Growth of Human Breast Cancer Cells in Athymic Mice," *J. Clin. Invest.* 84:1418–1423 (1989) copyright The American Society for Clinical investigation, Inc.

Arvidsson et al., "Tyr–716 in the Platelet–Derived Growth Factor β–Receptor Kinase Insert is Involved in GRB2 Binding and Ras Activation," *Molecular and Cellular Biology* 14:6715–6726 (1994) © The American Society for Microbiology.

Autrey and Tahk, "The Synthesis and Sterochemistry of Some Isatylideneacetic Acid Derivatives," *Tetrahedron* 23:901–917 (1967) ©Pegamon Press.

Bahner and Brotherton, "6–Dimethylaminochrysene and Other Analogs of 4–(4–Dimethylamino)stilbene," *J. Med. Chem.* 12:722–723 (1969).

Bahner et al., "Benzylideneidenes with Oxygen Attached to the Indene Ring," *J. Med. Chem.* 12:721–722 (1969).

Bamfield et al., "Diels–Alder Reactions of Oxindolylidenacetone," *J. Chem. Soc. (C)* 1028–1030 (1966).

Barbier, et al., "Synthesis of Isobrassilexin, A Biologically Active Isomer of Bassilexin, a Cruciferae Phytoalexin," *Synthetic Communciations* 23(22):3109–3117 (1993) © Marcel Dekker, Inc.

Baserga, "Oncogenes and the Strategy of Growth Factors," *Cell* 79:927–930 (1994) © Cell Press.

Baserga, "The Insulin–like Growth Factor I Receptor: A Key to Tumor Growth?" *Cancer Research* 55:249–252 (1995).

Beilstein Reg. No. 233511 (1997).

Beilstein Reg. No. 235647 (1997).

Beilstein Reg. No. 252929 (1998).

Benzies, et al., "2–Formyl–3–Methoxymethylindole, 3–Ethoxymethyl–2–Formylindoline and 2–Formyl–3–Methylindole," *Synthetic Communications:* 16(14), 1799–1807 (1986) © Mercel Dekker, Inc.

Blake and Jaques, "Anisotropic Effects in α–Substituted Methoxystilbenes," *J. Chem. Soc. Perkin II:* 1660–1663 (1973) © Pergamon, Oxford.

Bolen et al., "The Src family of tyrosine protein kinases in hemopoietic signal transduction," *FASEB J.* 6:3403–3409 (1992).

Bolen, "Nonreceptor tyrosine protein kinases," *Oncogene* 8:2025–2031 (1993) copyright MacMillan Press Ltd.

Bonner et al., "Structure and Biological Activity of Human Homologs of the raf/mil Oncogene," *Molecular and Cellular Biology* 5:1400–1407 (1985) © The American Society for Microbiology.

Borsche et al., "Über vielkernige kondensierte Systeme mit heterocyclischen Ringen. XIII.," *Liebigs Ann. Chem.* 550:160–174 (1941).

Buzzetti et al., "Cinnamamide Analogs as Inhibitors of Protein Tyrosine Kinases," *III Farmaco* 48:615–636 (1993).

Cance et al., "Novel Protein Kinases Expressed in Human Breast Cancer," *Int. J. Cancer* 54:571–577 (1993) © Wiley–Liss, Inc.

Canoira and Rodriguez, "Synthesis of Oxindole Derivatives from N–Alkenyl–o–Chloroanilides with Zero–Valent Nickel Complex," *J. Heterocyclic Chem.* 22:1511–1518 (1985).

Carpenedo et al., "Identification and Measurement of Oxindole (2–Indolinone) in the Mammalian Brain and Other Rat Organs," *Analytical Biochemistry* 244:74–79 (1997) © Academic Press, Inc.

Chao, "Growth Factor Signaling: Where Is the Specificity?" *Cell* 68:995–997 (1992) copyright Cell Press.

Chatten et al., "Substituted Oxindoles. Part VI. Polarographic Reduction of Substituted trans–3–Benzylideneindol–2(3H)–ones," *J. Chem. Soc. Perkin II:* 469–473 (1973).

Chatterjee, et al., "Acylation of Indoles by Duff Reaction and Vilsmeier–Haack Formylation and Conformation of N–Formylindoles," *J. Org. Chem.,* 38:4002–4004 ©The American Chemical Society.

Chen et al., "Effects of 3,3–Dipyridylmethyl–1–Phenyl–2–Indolinone on γ–Aminobutyric Acid Elicited Chloride Current of Snail Central Neuron," *Chinese Journal of Physiology* 40:149–156 (1997).

Calesson–Welsh, "Signal Transduction by the PDGF Receptors," *Progress in Growth Factor Research* 5:37–54 (1994) © Elsevier Science Ltd.

Coda et al., "(Z)– and (E)–Arylidene–1, 3–dihydroindol–2–ones: Configuration, Conformation and Infrared Carbonyl Stretching Frequencies," *J. Chem. Soc. Perkin Trans. II:* 615–619 (1984).

Coda et al., "3–(4–methylbenzilidene)–1,3–dihydroindole–2–one," *Journal of the Chemical Society, Perkin Transactions 2* 4:615–620 (1984) Database Crossfire, Beilstein Reference No. 6–21.

Coppola et al., "A Functional Insulin–Like Growth Factor I Receptor Is Required for the Mitogenic and Transforming Activities of the Epidermal Growth Factor Receptor," *Molecular and Cellular Biology* 14:4588–4595 (1994) © The American Society for Microbiology.

Daisley and Walker, "Thin–layer chromatographic separation of some substituted 3–benzylidine–indol–2(3H)–ones," *J. Chromatography* 100:240–242 (1974) © Elsevier Scientific Publishing Company.

Damiani et al., "Inhibition of Copper–Mediated Low Density Lipoprotein Peroxidation by Quinoline and Indolinone Nitroxide Radicals," *Biochemical Pharmacology* 48:1155–1161 (1994) copyright Elsevier Science Ltd.

Dati et al., "Inhibition of c–erbB–2 oncogene expression by estrogens in human breast cancer cells," *Oncogene* 5:1001–1006 (1990).

Davis et al., "Synthesis and Microbiological Properties of 3–Amino–1–Hydroxy–2–Indolinone and Related Compounds," *Journal of Medicinal Chemistry* 16:1043–1045 (1973) ©American Chemical Society.

De Vries et al., "The fms–Like Tyrosine Kinase, a Receptor for Vascular Endothelial Growth Factor," *Science* 255:989–991 (1992).

Decker and Lohmann–Matthes, "A quick and simple method for the quantitation of lactate dehydrogenase release in measurements of cellular cytotoxicity and tumor necrosis factor (TNF) activity," *J. Immunol. Methods* 15:61–69 (1988) copyright Elsevier.

Decodts et al., "Sucide inhibitors of proteases. Lack of halomethyl derivatives of some aromatic lactams," *Eur. J. Med. Chem* 18:107–111 (1983).

Desimoni et al., "Catalysis with Inorganic Cations. $V^1$ Intramolecular Hetero Diels–Alder versus Ene Reactions: Effect of Magnesium perchlorate on Chemoselectivity," *Tetrahedron* 52(36) 12009–12018 (1196) © Pergamon.

Dickson et al., "13. Tyrosine kinase receptor—nuclear protooncogene interactions in breast cancer," *Cancer Treatment Res.* 61:249–273 (1992) © Kluwer Academic Publishers.

Elliott and Rivers, "Reduction of Some Oxindolylidene Derivatives to 3–Substituted Oxindoles by Sodium Borohydride," *J. Med. Chem.* 29:2438–2440 (1964).

Elliott et al., "1–methyl–2–(3–oxindolidenmethyl)– pyridinium," *Journal of Organic Chemistry* 29:2438–2440 (1964) Database Crossfire, Beilstein Reference No. 5–24.

Fantl et al., "Distinct Phosphotyrosines on a Growth Factor Receptor Bind to Specific Molecules That Mediate Different Signaling Pathways," *Cell* 69:413–423 (1992) © Cell Press.

Fendly et al., Characterization of Murine Monoclonal Antibodies Reactive to Either the Human Epidermal Growth Factor Receptor or HER2/neu Gene Product, *Cancer Research* 50:1550–1558 (1990);@ American Association for Cancer Research.

Ferrara and Henzel, "Pituitary Follicular Cells Secrete a Novel Heparin–Binding Growth Factor Specific for Vascular Endothelial Cells," *Biochemical and Biophysical Research Communications* 161:851–858 (1989) © Academic Press, Inc.

Fingl and Woodbury, "Chapter 1—General Principles," In *The Pharmacological Basis of Therapeutics* 5th edition, Goodman and Gilman editors, MacMillan Publishing Co., Inc., New York, pp. 1–46 (1975) © MacMillan Publishing Co. Inc.

Fischer, "The Pyrroles, Paper 4: Pyrrole Aldehyde (Ii) And Pyrrole Nitrile," *W. Chemische Berichte*, 55:519–527, 1923.

Floege et al., "Factors involved in the regulation of mesangial cell proliferation in vitro and in vivo," *Kidney International* 43:S47–S54 (1993) © International Society of Nephrology.

Floege et al., "Heparin suppresses mesangial cell proliferation and matrix expansion in experimental mesangioproliferative glomerulonephritis," *Kidney International* 43:369–380 (1993) © International Society of Nephrology.

Folkman and Shing, "Angiogenesis," *J. Biol. Chem.* 267:10931–10934 (1992) © The American Society for Biochemistry and Molecular Biology.

Folkman "Ch. 24. Angiogenesis," *Congress of Thrombosis and Haemostasis* (Verstraete et al., eds.) Leuven University Press, Leuven pp. 583–596 (1987).

Folkman "Tumor Angiogenesis: Therapeutic Implications," *New England J. Medicine* 285:1182–1186 (1971).

Folkman, "What is the Evidence that Tumors are Angiogenesis Dependent?" *Journal of the National Cancer Institute* 82:4–6 (1990).

Folkman, "Angiogenesis in Psoriasis: Therapeutic Implications," *J. Invest. Dermatol.* 59:40–43 (1973) copyright The Williams & Wilkins Co.

Gazit et al., "Tyrphostins. 2. Heterocyclic and α–Substituted Benzylidenemalononitrile Tyrphostins as Potent Inhibitors of EGF Receptor and ErbB2/neu Tyrosine Kinases," *J. Med. Chem.* 34:1896–1907 (1991) copyright Am. Clem. Soc.

Gennaro (editor), *Remington's Pharmaceutical Sciences* (1990) (Table of Contents Only).

Goldring and Goldring, "Cytokines and Cell Growth Control," *Critical Reviews in Eukaryotic Gene Expression* 1:301–326 (1991).

Gottardis et al., "Estradiol–Stimulated Growth of MCF–7 Tumors Implanted in Athymic Mice: A Model to Study the Tumoristatic Action of Tamoxifen," *J. Steroid Biochem.* 30:311–314 (1988) © Pergamon Press.

Graziani et al., "Hepatocyte Growth Factor/Scatter Factor Stimulates the Ras–Guanine Nucleotide Exchanger," *The Journal of Biological Chemistry* 268:9165–9168 (1993) ©American Society for Biochemistry and Molecular Biology.

Hayler et al., Development of Large–Scale Syntheses of Ropinirole in the Pursuit if a Manufacturing Process, *Organic Process Research & Development* 2(1) 3–9 (1998) ©The American Chemical Society and Royal Society of Chemistry.

Hewgill and Stewart, "Phenanthrene–4,5–quinones: a Synthesis of Morphenol," *J. Chem. Soc. Perkin Trans. I*:1305–1311 (1988).

Hirao et al., "Rhodium–Catalyzed Carbonylation of 2–Alkynylaniline: Syntheses of 1,3–Dihydroindol–2–ones," *Tetrahedron Letters* 36(35) 1995 ©Pergamon.

Hodges et al., "Chemical and biological properties of some oxindolidyl–3–methines," *Canadian J. Chemistry* 46:2189–2194 (1968).

Honegger et al., "Point Mutation at the ATP Binding Site of EGF Receptor Abolishes Protein–Tyrosine Kinase Activity and Alters Cellular Routing," *Cell* 51:199–209 (1987) © Cell Press.

Houck et al., "Dual Regulation of Vascular Endothelial Growth Factor Bioavailability by Genetic and Proteolytic Mechanisms," *J. Biol. Chem.* 267:26031–26037 (1992)© American Society for Biochemistry and Molecular Biology, Inc.

Howard et al., "Synthesis and aldose reductase inhibitory activity of substituted 2(1H)–benzimidazolone–and oxindole–1–acetic acids," *Eur. J. Med. Chem.* 27:779–789 (1992) © Elsevier, Paris.

Hu et al., "Interaction of Phosphatidylinositol 3–Kinase–Associated p85 with Epidermal Growth Factor and Platelet–Derived Growth Factor Receptors," *Molecular and Cellular Biology* 12:981–990 (1992) copyright Am. Soc. Microbiol.

Ijaz et al., "The Conversion of o,β–Dinitrostyrenes into Indoles and the Preparation of Oxindole Quinones," *J. Chem. Res. (S)*: 116 (1990).

Jellinek et al., "Inhibition of Receptor Binding by High–Affinity RNA Ligands ot Vascular Endothelial Growth Factor," *Biochemistry* 33:10450–10456 (1994) © American Chemical Society.

Kashishian and Cooper, "Phosphorylation Sites at the C–terminus of the Platelet–Derived Growth Factor Receptor Bind Phospholipase Cγ1," *Molecular Biology of the Cell* 4:49–57 (1993) © The American Society for Cell Biology.

Kashishian et al., "Phosphorylation sites in the PDGF receptor with different specificities for binding GAP and P13 kinase in vivo," *The EMBO Journal* 11:1373–1382 (1992).

Kato et al., "Simultaneous Determination of Amfenac Sodium and its Metabolite (7–Benzoly–2–Oxindole) in Human Plasma by High–Performance Liquid Chromatography," *Journal of Chromatography* 616:67–71 (1993) © Elsevier Science.

Katritzky et al., "Color and Constitution. Part 8[1]. Some Novel Dyestuffs Containing Indoxyl Residues," *J. Heterocyclic Chem.* 25:1287–1292 (1988).

Kazlauskas et al., "The 64–kDa protein that associates with the platelet–derived growth factor receptor β subunit via Tyr–1009 is the SH2–containing phosphotyrosine phosphatase Syp," *Proc. Natl. Acad. Sci. USA* 90:6939–6942 (1993).

Kendall and Thomas, "Inhibition of vascular endothelial cell growth factor activity by an endogenously encoded soluble receptor," *Proc. Natl. Acad. Sci. USA* 90:10705–10709 (1993).

Khalil and Abdel–Rahman, "Synthesis of New Mero– and Asymmetrical Pyrazolo–Monomethine Cyanine Dyes," *J. Indian Chem. Soc.* 54:904–907 (1977) ©The Indian Chemical Society.

Kikumoto et al., "The Reactions of Oxindoles and Isatin with Nitrobenzyl Chlorides," *Tetrahedron* 22: 3337–3343 (1966) ©Pergamon Press Ltd.

Kim et al., "Inhibition of vascular endothelial growth factor–induced angiogenesis suppresses tumour growth in vivo," *Nature* 362:841–844 (1993).

Kinsella et al., "Protein Kinase C Regulates Endothelial Cell Tube Formation on Basement Membrane Matrix, Matrigel," *Exp. Cell Research* 199:56–62 (1992) © Academic Press, Inc.

Klagsbrun and Soker, "VEGF/VPF; the angiogenesis factor found?" *Current Biology* 3:699–702 (1993) ©Current Biology.

Kobayashi et al., "Antitumor Activity of Indole Derivatives," *Yakugaku Zasshi* 97:1033–1039 (1977).

Koch et al., "SH2 and SH3 Domains: Elements That Control Interactions of Cytoplasmic Signaling Proteins," *Science* 252:668–674 (1991).

Kohler and Milstein, "Continuous cultures of fused cells secreting antibody of predefined specificity," *Nature* 256:495–497 (1975).

Komada and Kitamura, "The cell dissociation and motility triggered by scatter factor/hepatocyte growth factor are mediated through the cytoplasmic domain of the c–Met receptor," *Oncogene* 8:2381–2390 (1993).

Korc et al., "Overexpression of the Epidermal Growth Factor Receptor in Human Pancreatic Cancer Is Associated with Concomitant Increases in the Levels of Epidermal Growth Factor and Transforming Growth Factor Alpha," *J. Clin. Invest.* 90:1352–1360 (1992) copyright The American Society for Clinical Investigation, Inc.

Korzeniewski and Callewaert, "An Enzyme–Release Assay for Natural Cytotoxicity," *J. Immunol. Methods* 64:313–320 (1983) © Elsevier Science Publishers.

Kovac and Stetinova, "Furan derivatives. LXXX. Synthesis and properties of substituted furfurylidenoxindoles," *Chem. rvesu* 30:484–492 (1976).

Krueger and Saito, "A human transmembrane protein–tyrosine–phosphatase, PTPb, is expressed in brain and has an N–terminal receptor domain homologous to carbonic anhydrases," *Proc. Natl. Acad. Sci. USA* 89:7417–7421 (1992).

Kumbae et al., "Amplification of αplatelet–derived growth factor receptor gene lacking an exon coding for a portion of the extracellular region in a primary brain tumor of glial origin," *Oncogene* 7:627–633 (1992).

Lal et al., "Novel Diuretic Agents: Syntheses of Substituted Isatylidenes & 3–Alkyl or 3–Arylalkyl–2–oxindoles," *Indian Journal of Chemistry* 13: 898–903 (1975).

Larock and Babu, "Synthesis of Nitrogen Heterocycles via Palladium–catalyzed Intramolecular Cyclization," *Tetrahedron Letters* 28:5291–5294 (1987) copyright Pergamon Journals Ltd.

Lee and Donoghue, "Intracellular Retention of Membrane–Anchored v–sis Protein Abrogates Autocrine Signal T transduction," *J. Cell. Biol.* 118:1057–1070 (1992) ©The Rockefeller University Press.

Levitzki and Gazit, "Tyrosine Kinase Inhibition: An Approach to Drug Development," *Science* 267:1782–1788 (1995).

Maass et al., "Viral Resistance to the Thiazolo–Iso–Indolinones, a New Class of Nonnucleoside Inhibitors of Human Immunodeficiency Virus Type 1 Reverse Transcriptase," *Antimicrobial Agents and Chemotherapy* 37:2612–2617 (1993) ©American Society for Microbiology.

Macaulay et al., "Autocrine Function for Insulin–line Growth Factor I in Human Small Cell Lung Cancer Cell Lines and Fresh Tumor Cells," *Cancer Research* 50:2511–2517 (1990).

Mariani et al., "Inhibition of angiogenesis by FCE 26806, a potent tyrosine kinase inhibitor," *Experimental Therapeutics—Proceedings of the American Association for Cancer Research* 35:381 at abstract No. 2268 (Mar. 1994).

Martin–Leon et al., "On the Cyclization to the Elusive Amino–4H–pyran Ring Some New Facts," *Liebigs Ann. Chem.* 101–104 (1990) copyright VCH Veilaxs of Sellschaft mbH ©VCH.

Mel'Nikova TV et al., "Indole chemistry. XXXVIII. Cleavage of a carbon–carbon bond during the reaction of 2–aminiinoindoles with difunctional compounds," *Chemical Abstracts* 80 (1974) Abstract No. 003413.

Millauer et al., "High Affintiy VEGF Binding and Developmental Expression Suggest Flk–1 as a Major Regulator of Vasculogenesis and Angiogenesis," *Cell* 72:835–846 (1993) © Cell Press.

Mohammadi et al., "Structures of the Tyrosine Kinase Domain of Fibroblast Growth Factor Receptor in Complex with Inhibitors," *Science* 276:955–960 (1997) © American Association for the Advancement of Science.

Moreto et al., "Study of the Laxative Properties of the Disodium Slat of the Sulfuric Diester of 3,3 Bis–(4–Hydroxyphenyl)–7–Methyl–2–Indolinone (DAN–603) in the Rat," *European Journal of Pharmacology* 36:221–226 (1976) ©North–Holland Publishing Company.

Moreto et al., "3,3–Bis–(4–Hydroxyphenyl)–7–Methyl–2–Indolinone (BHMI), the Active Metabolite of the Laxative Sulisatin," *Arzneimittel–Forschung Drug Research* 29:1561–1564 (1979).

Morrison et al., "Signal Transduction From Membrane to Cytoplasm: Growth Factors and Membrane–Bound Oncogene Products Increase Raf–1 Phosphorylation and Associated Protein Kinase Activity," *Proc. Natl. Acad. Sci. USA* 85:8855–8859 (1988).

Mosmann, "Rapid Colorimetric Assay for Cellular Growth and Survival: Application to Proliferation and Cytotoxicity Assays," *J. Immunol. Methods* 65:55–63 (1983) copyright Elsevier Publishers B.V.

Neber and Röcker, "On the action of benzaldehydes on the free o–aminophenylacetic acid (II)," *Chem. Ber.* 56:1710–1716 (1923) (English Translation).

Nishimura et al., "Two Signaling Molecules Share a Phosphotyrosine–Containing Binding Site in the Platelet–Derived Growth Factor Receptor," *Molecular and Cellular Biology* 13:6889–6896 (1993).

Nodiff et al., "Antimalarial Phenanthrene Amino Alcohols. 1. Fluorine–Containing 3– and 6–Substituted 9–Phenanthrenemethanols," *J. Med. Chem.* 14:921–925 (1971).

Nodiff et al., "Antimalarial Phenanthrene Amino Alcohols. 3. Halogen–containing 9–phenanthrenemethanols," *Chemical Abstracts,* vol. 83, abstract No. 188214 (1975).

Osborne et al., "Effect of Estrogens and Antiestrogens on Growth of Human Breast Cancer Cells in Athymic Nude Mice," *Cancer Research* 45:584–590 (1985).

O'Sullivan and Rothery, "The Preparation and Possible Clinical Significance of 4'-Dialkylaminoisoindogenides," *Clinica Chimica Acta* 62:181–182 (1975) ©Elsevier Scientific Publishing Company.

Ozzello and Sordat, "Behavior of Tumors Produced by Transplantation of Human Mammary Cell Lines in Athymic Nude Mice," *Eur. J. Cancer* 16:553–559 (1980).

Pavlenko et al., "Introduction of aminomethyl groups into heterocyclic CH–acid molecules," *Dopov. Akad. Nauk Ukr Rsrs, Ser. B: Geol., Khim. Biol. Nauki* 7:64–66 (1980) We should add thqat we are Sub. Abstract.

Perkin et al., "Harmine and Harmaline. Part II. The Synthesis of isoHarman," *J. Chem. Soc.* 103:1973–1985 (1913).

Plate et al., "Vascular endothelial growth factor is potential tumor angiogenesis factor in human gliomas in vivo," *Nature* 359:845–848 (1992).

Plowman et al., "Receptor Tyrosine Kinases as Targets for Drug Intervention," *DN& P* 7:334–339 (1994).

Quallich et al., A General Oxindole Synthesis, *J. Synthetic Organic Chemistry:* 51–51 (1993).

Quinn et al., "Fetal liver kinase 1 is a receptor for vascular endothelial growth factor and is selectively expressed in vascular endothelium," *Proc. Natl. Acad. Sci. USA* 90:7533–7537 (1993).

Rozakis–Adcock et al., "Association of the Shc and Grb2/Sem5 SH2–containing proteins is implicated in activation of the Ras pathway by tyrosine kinases," *Nature* 360:689–692 (1992).

Ruveda and Gonzalez, "Geometric isomerism in benzylideneoxindoles," *Spectrochimica Acta* 26A: 1275–1277 (1970).

Rygaard and Povlsen, "Heterotransplantation of a Human Malignant Tumour to 'Nude' Mice," *Acta Path. Microbiol. Scand.* 77:758–760 (1969).

Sainsbury et al., "Electrochemical Oxidation of Aromatic Ethers. Part 5.[1] Further Studies of the Coupling Reactions of Alkoxylated Aralkyl– and Aryl–amides," *J.C.S. Perkin I* 108–114.

Saito and Streuli, "Molecular Characterization of Protein Tyrosine Phosphatases," *Cell Growth & Differentiation* 2:59–65 (1991) ©Molecular Biolody Journal of the American Association for Cancer Research.

Sandberg–Nordqvist et al., "Characterization of Insulin–Like Growth Factor 1 in Human Primary Brain Tumors," *Cancer Research* 53:2475–2478 (1993).

Schindler et al., "Über Dibenz[b,f]–azocin–Derivate," *Helvetica Chimica Acta* 49:985–989 (1966).

Schlessinger and Ullrich, "Growth Factor Signalling by Receptor Tyrosine Kinases," *Neuron* 9:383–391 (1992) © Cell Press.

Schuchter et al., "Successful Treatment of Murine Melanoma with Bryostatin 1," *Cancer Research* 51:682–687 (1991).

Seibert et al., "Clonal Variation of MCF–7 Breast Cancer Cells in Vitro and in Athymic Nude Mice," *Cancer Research* 43:2223–2234 (1983).

Shafie and Grantham, "Role of Hormones in the Growth and Regression of Human Breast Cancer Cells (MCF–7) Transplanted Into Athymic Nude Mice," *J. Natl. Cancer Institute* 67:51–56 (1981).

Shibuya et al., "Nucleotide sequence and expression of a novel human receptor–type tyrosine kinase gene (flt) closely relted to the fms family," *Oncogene* 5:519–524 (1990).

Shiraishi et al., "Specific inhibitors of Tyrosine–Specific Protein Kinase, Synthetic 4–Hydroxycinnamamide Derivatives," *Biochemical and Biophysical Research Communications* 147:322–328 (1987) ©Academic Press.

Shiraishi et al., "Specific Inhibitors of Tyrosine–specific Protein Kinases: Properties of 4–Hydroxycinnamamide Derivatives in Vitro," *Cancer Research* 49:2374–2378 (1989).

Shweiki et al., "Vascular endothelial growth factor induced by hypoxia may mediate hypoxia–initiated angiogenesis," *Nature* 359:843–845 (1992).

Singh et al., "Indolinone Derivatives as Potential Antimicrobial Agents," *Zentralbl. Microbiol.* 144:105–109 (1989) copyright VEB Gustav Fischer Veriag Jena.

Singh et al., "Synthesis and Anticonvulsant Activity of New 1–Substituted 1'–Methyl–3–Chloro–2–Oxospiro (Azetidin–3', 4–Indol–2' Ones)," *Bollettino Chimico Farmaceutico* 133:76–79 (1994).

Skehan et al., "New Colorimetric Cytotoxicity Assay for Anticancer–Drug Screening," *J. Natl. Cancer Inst.* 82:1107–1112 (1990).

Slamon et al., "Studies of the HER–2/neu Proto–oncogene in Human Breast and Ovarian Cancer," *Science* 244:707–712 (1989).

Soldi et al., "Platelet–Activating Factor (PAF) Induces the Early Tyrosine Phosphorylation of Focal Adhesion Kinase (p125$^{FAK}$) in Human Endothelial Cells," *Oncogene* 13:515–525 (1996) copyright Stockton Press.

Songyang et al., "SH2 Domains Recognize Specific Phosphopeptide Sequences," *Cell* 72:767–778 (1993) © Cell Press.

Songyang et al., "Specific Motifs Recognized by the SH2 Domains of Csk, 3BP2, fps/fes, GRB–2, HCP, SHC, Syk and Vav," *Molecular and Cellular Biology* 14:2777–2785 (1994) © American Society for Microbiology.

Spada, et al., "Small molecule inhibitors of tyrosine kinase activity," *Expert Opinion on Therapeutic Patents* 5:805–817 (1995) © Ashley Publications.

Stetinova et al., "Stereochemistry and Photoisomerisation of Furfurylideneoxindoles," *Collection Czechoslov. Chem. Commun.* 42:2201–2206 (1977).

Stolle, Beilstein Reg. No. 273650, *J. Prakt. Chem.,* vol. 2, p. 128 (1930).

Stolle, Beilstein Reg. No. 305045, *J. Prakt, Chem.,* vol. 2, p. 128 (1930).

Sumpter and Miller, "Chapter IV—Oxindole," *Heterocyclic Compounds With Indole and Carbazole Systems,* © Interscience Publishers, Inc., New York, pp. 134–153 (1954).

Sun et al., "Design, Synthesis, and Evaluations of Substituted 3–[(3– or 4–Carboxyethylpyrrol–2–yl) methylidenyl] indolin–2–ones as Inhibitors of VEGF, FGF, and PDGF Receptor Tyrosine Kinases," *Journal of Medicinal Chemistry* 42:5120–5130 (1999) ©American Chemical Society.

Sun et al, "Synthesis and Biological Evaluations of 3–Substitued Indolin–2–ones: A Novel Class of Tyrosine Kinase Inhibitors That Exhibit Selectivity toward Particular Receptor Tyrosine Kinases," *J. Med. Chem.* 41:2588–2603 (1998) © The American Chemical Society.

Superti–Furga et al., "A functional screen in yeast for regulators and antagonizers of heterologous protein tyrosine kinases," *Nature Biotech.* 14:600–605 (1996).

Superti–Furga et al., "Csk inhibition of c–Src activity requires both the SH2 and SH3 domains of Src," *EMBO J.* 12:2625–2634 (1993) © Oxford University Press.

Tacconi and Marinone, "Preparazione e caratteristiche di alcuni 3–ossindolidenderivati," *Ricerca Scientifica* 38:1239–1244 (1968).

Tacconi et al., "(Z)– and (E)–3–Alkylidene–1, 3–dihydroindol–2–ones: Influence of Configuration on the Transmission of the Inductive Effect ot the Carbonyl Group," *J.C.S. Perkin II* 150–154 (1976).

Takano et al., "Inhibition of angiogenesis by a novel diaminoanthraquinone that inhibits Protein Kinase C," *Mol. Bio. Cell* 4:358A at abstract No. 2076 (1993).

Terrett et al., "Combinatorial Synthesis—The Design of Compound Libraries and Their Application to Drug Discovery," *Tetrahedron* 51(30):8135–8173 (1995) copyright Pergamon! all even pages missing!.

Thio et al., "The Interconversion of 2–(2–Aminophenyl)–3–piperolidinone and 3–(2–piperidylmethyl)– 2–indolinone: A Reversible N=N' Transacylation," *Notes* (1971) 479–482.

Thompson et al., "Facile Dimerisation of 3–Benzylideneindolin–2–thiones," *J. Chem. Soc. Perkin Trans.* (*I*) 1835–1837 (1993).

Torp et al., "Expression of the Epidermal Growth Factor Receptor Gene in Human Brain Metastases," *APMIS* 100:713–719 (1992).

Traxler, "Protein tyrosine kinase inhibitors in cancer treatment," *Expert Opinion on Therapeutic Patents* 7(6):571–588 (1997) © Ashley Publications Ltd.

Treibs et al., "Über isoindigoide Farbstoffe der Pyrrol–Reihe," *Liebigs Ann. Chem.* 702:112–130 (1967).

Tsai et al., "The Effect of 3,3–Di–Pyridyl Methyl–1–Phenyl–2–Indolinone on the Nerve Terminal Currents of Mouse Skeletal Muscles," *Neuorpharmacology* 31:943–947 (1992) ©Pergamon Press.

Tuzi et al., "Expression of growth factor receptors in human brain tumours," *Br. J. Cancer* 63:227–233 (1991).

Twamley–Stein et al., "The Src family tyrosine kinases are required for platelet–derived growth factor–mediated signal transduction in NIH 3T3 cells," *Proc. Natl. Acad. Sci. USA* 90:7696–7700 (1993).

Ullrich and Schlessinger, "Signal Transduction by Receptors with Tyrosine Kinase Activity," *Cell* 61:203–212 (1990) copyright Cell Press.

Vaisman et al., "Characterization of the Receptors for Vascular Endothelial Growth Factor," *J. Biol. Chem.* 265:19461–19466 (1990) © The American Society for Biochemistry and Molecular Biology.

Varma and Gupta, "Nucleophilic Reactions of 2–Methyl–3–(4'–carbomethoxyphenyl)–4–quinazolinones with 2–Indolinones," *J. Indian Chem. Soc.* 66:804–805 (1989) © The Indian Chemical Society.

Voller et al., "Ch. 45—Enzyme–Linked Immunosorbent Assay," in *Manual of Clinical Immunology*, 2$^{nd}$ edition, Rose and Friedman editors, American Society of Microbiology, Washington, D.C., pp. 359–371 (1980); @American Society for Microbiology.

Wahl et al., "3–benzilidene–5–methyl–1, 3–dihydroindol–2–one," *Ann. Chim.* 350 (1926), Database Crossfire, Beilstein Reference No. 2–21–00–00290.

Wahl et al., "Chimie Organique—Sur les iso–indogenides," *C.R. Hebd. Seances Acad. Sci.* 149:132–134 (1909).

Wahl, Beilstein Reg. No. 191439, *Bull. Soc. Chim. Fr.,* p. 1038 (1909).

Wahl, Beilstein Reg. No. 231732, *Bull. Soc. Chim. Fr.,* p. 1035–1038 (1909).

Walker, "Synthesis of a α–(p–Aminophenyl)– and α–(p–Chlorophenyl)–β–aryl–propionitriles by Catalytic Reduction of Stilbenenitriles," *J. Med. Chem.* 8:583–588 (1965).

Walker et al., "Synthesis of New 3–(Pyridylmethylene)–, 3–(Pyridylmethyl)–, 3–(Piperidylmethyl)–, and 3–(β–Alkylaminoethyl)–2–indolinones. The Reduction of Isoindogenides, Nitro Compounds, and Pyridines in a Series of 2–Indolinones," *J. Med. Chem.* 8:626–637 (1965).

Warri et al., "Estrogen Suppression of erbB2 Expression is Associated with Increased Growth Rate of ZR–75–I Human Breast Cancer Cells In Vitro and in Nude Mice," *Int. J. Cancer* 49:616–623 (1991) © Wiley–Leiss, Inc.

Weidner et al., "Tumor Angiogenesis and Metastais—Correlation in Invasive Breast Carcinoma," *New England J. Medicine* 324:1–7 (1991) © Massachusetts Medical Society.

Winkelmann et al., "Chemotherapeutically Active Nitro Compounds: 4. 5–Nitroimidazoles (Part I)," *Arzneim.–Forsch./Drug Res.* 27:2251–2263 (1977).

Wright et al., "Cyclic Hydroxamic Acids Derived from Indole," *J. Am. Chem. Soc.* 78:221–224 (1956).

Wright et al., "Inhibition of Angiogenesis in Vitro and In Ovo With an Inhibitor of Cellular Protein Kinases, MDL 270932," *J. Cellular Physiology* 152:448–457 (1992).

Young and Babbitt, "2–(2–Methyl–3–indolyl)–1,4–benzoquinone, a Reversible Redox Substrate at the Carbon–Paste Elctrode in Acidic Aqueous–Ethanolic Media," *J. Org. Chem.* 47:1571–1572 (1982) copyright Am. Chem. Soc.

Zaman et al., "Tyrosine Kinase Activity of Purified Recombinant Cytoplasmic Domain of Platlet–Derived Growth Factor β–Receptor (β–PDGFR) and Discovery of a Novel Inhibitor of Receptor Tyrosine Kinases," *Biochemical Pharmacology* 57:57–64 (1999) ©Elsevier Science Inc.

Zhang et al., "Microtubule Effects of Welwistatin, a Cyanobacterial Indolinone that Circumvents Multiple Drug Resistance," *Molecular Pharmacology* 49:228–234 (1996) ©The American Society for Pharmacology and Experimental Pharmaceutics.

Zhungietu et al., "Reaction of Indoles and 2–Ketoindolines With Some Aldehydes," *Chemical Abstracts,* vol. 78, abstract No. 111201 (1990).

3-[4-SUBSTITUTED HETEROCYCLYL)-PYRROL-2-YLMETHYLIDENE]-2-INDOLINONE DERIVATIVES AS KINASE INHIBITORS

CROSS-REFERENCE TO RELATED APPLICATIONS

This application is related to, and claims priority from, provisional Application Serial No. 60/328,226, filed Oct. 10, 2001, which is incorporated by reference herein in its entirety.

BACKGROUND OF THE INVENTION

1. Field of Invention

The present invention is directed to certain 3-[4-(substituted heterocyclyl)-pyrrol-2-ylmethylidene]-2-indolinone derivatives that inhibit kinases, in particular VEGFR, PDGFR, and c-kit kinases. Pharmaceutical compositions comprising these compounds, methods of treating diseases mediated by kinases, in particular VEGFR, PDGFR, and/or c-kit kinases, utilizing pharmaceutical compositions comprising these compounds, and methods of preparing them are also disclosed.

2. State of the Art

Protein kinases (PKs) are enzymes that catalyze the phosphorylation of hydroxy groups on tyrosine, serine and threonine residues of proteins. The consequences of this seemingly simple activity are staggering; cell growth, differentiation and proliferation, i.e., virtually all aspects of cell life in one way or another depend on PK activity. Furthermore, abnormal PK activity has been related to a host of disorders, ranging from relatively non life threatening diseases such as psoriasis to extremely virulent diseases such as glioblastoma (brain cancer) (see U.S. Pat. No. 5,792,783 which is incorporated herein by reference in its entirety). For example, VEGFR and/or PDGFR kinases are involved in various cancers such as T-cell lymphoma, acute lymphoblasitc leukemia, acute myeloid leukemia, melanoma, glioblastoma and others (see Bellamy W. T. et al., Cancer Res. 1999, 59, 728–733). VEGF also plays a role in ocular diseases such as diabetic retinopathy, retinal ischemia, and retinal neovascularization.

In view of the apparent link between PK-related cellular activities and a wide variety of human disorders, a great deal of effort is being expended in an attempt to identify ways to modulate PK activity. Some of this effort has involved biomimetic approaches using large molecules patterned on those involved in the actual cellular processes (e.g., mutant ligands (U.S. Pat. No. 4,966,849); soluble receptors and antibodies (App. No. WO 94/10202, Kendall and Thomas, Proc. Nat'l Acad. Sci., 90:10705–09 (1994), Kim, et al., Nature, 362:841–844 (1993)); RNA ligands (Jelinek, et al., Biochemistry, 33:10450–56); Takano, et al., Mol. Bio. Cell 4:358A (1993); Kinsella, et al., Exp. Cell Res. 199:56–62 (1992); Wright, et al., J. Cellular Phys., 152:448–57) and tyrosine kinase inhibitors (WO 94/03427; WO 92/21660; WO 91/15495; WO 94/14808; U.S. Pat. No. 5,330,992; Mariani, et al., Proc. Am. Assoc. Cancer Res., 35:2268 (1994)).

In addition to the above, attempts have been made to identify small molecules which act as PK inhibitors. For example, bis-monocylic, bicyclic and heterocyclic aryl compounds (PCT WO 92/20642), vinyleneazaindole derivatives (PCT WO 94/14808) and 1-cyclopropyl-4-pyridylquinolones (U.S. Pat. No. 5,330,992) have been described as tyrosine kinase inhibitors. Styryl compounds (U.S. Pat. No. 5,217,999), styryl-substituted pyridyl compounds (U.S. Pat. No. 5,302,606), quinazoline derivatives (EP App. No.0 566 266 A1), selenaindoles and selenides (PCT WO 94/03427), tricyclic polyhydroxylic compounds (PCT WO 92/21660), benzylphosphonic acid compounds (PCT WO 91/15495) and indolinone compounds (U.S. Pat. No. 5,792,783) have all been described as PTK inhibitors useful in the treatment of cancer. However these compounds have limited utility because of toxicity and/or poor bioavailability. Accordingly, there is a need for compounds that do not suffer from such drawbacks. The compounds of the present invention fulfil this need.

SUMMARY OF THE INVENTION

In one aspect, the preferred embodiments of the present invention relate to a compound of Formula (IV):

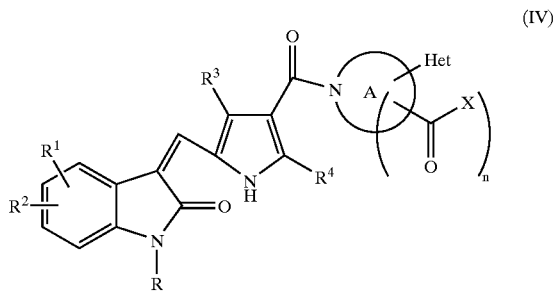

(IV)

wherein:

R is:
 (a) hydrogen;
 (b) —PO(OR$^5$)$_2$ where each R$^5$ is independently hydrogen or alkyl;
 (c) —COR$^6$ where R$^6$ is alkyl; or
 (d) —CHR$^7$NR$^8$R$^9$ where R$^7$ is hydrogen or alkyl, and R$^8$ and R$^9$ are independently hydrogen or alkyl; or R$^8$ and R$^9$ together with the nitrogen atom to which they are attached form a heterocycloamino ring;

R$^1$ is hydrogen, alkyl, alkoxy, hydroxy, trifluoromethyl, trifluoromethoxy, F, Cl, Br, or I;

R$^2$ is hydrogen, alkyl, heteroaryl, alkoxy, hydroxy, F, Cl, Br, or I;

R$^3$ is hydrogen or alkyl;

R$^4$ is hydrogen or alkyl;

ring A is optionally substituted heterocycloamino;

Het is cycloalkylaminoalkyl, cycloalkylalkylaminoalkyl, heteroaryl, heterocycle, heterocyclylcarbonylalkyl, heterocyclylalkylcarbonyl, or heterocyclylalkyl;

X is NR$_8$R$_9$ or OR$_8$; and n is 0 or 1; or a pharmaceutically acceptable salt thereof.

In another aspect, the present invention relates a compound of Formula (I):

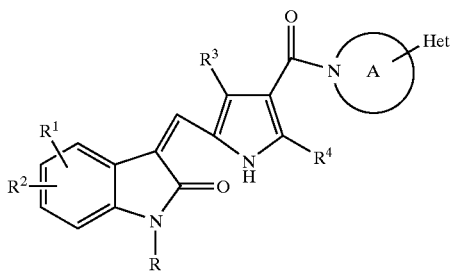

(I)

wherein:
R is:
(a) hydrogen;
(b) —PO(OR$^5$)$_2$ where each R$^5$ is independently hydrogen or alkyl;
(c) —COR$^6$ where R$^6$ is alkyl; or
(d) —CHR$^7$NR$^8$R$^9$ where R$^7$ is hydrogen or alkyl, and R$^8$ and R$^9$ are independently hydrogen or alkyl; or R$^8$ and R$^9$ together with the nitrogen atom to which they are attached form a heterocycloamino ring;
R$^1$ is hydrogen, alkyl, heteroaryl, alkoxy, hydroxy, trifluoromethyl, trifluoromethoxy, F, Cl, Br, or I;
R$^2$ is hydrogen, alkyl, alkoxy, hydroxy, F, Cl, Br, or I;
R$^3$ is hydrogen or alkyl;
R$^4$ is hydrogen or alkyl;
ring A is optionally substituted heterocycloamino;
Het is cycloalkylaminoalkyl, cycloalkylalkylaminoalkyl, heteroaryl, heterocycle, or heterocyclylalkyl; or
a pharmaceutically acceptable salt thereof.

In still another aspect, the preferred embodiments of the present invention relate to a compounds of Formula (I) or (IV):

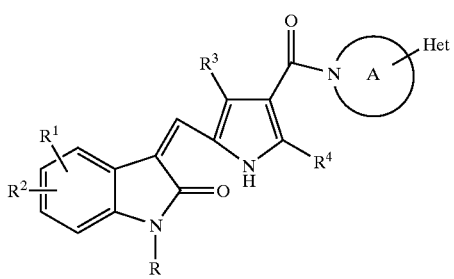

(I)

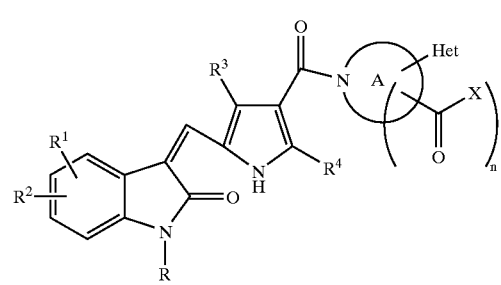

(IV)

wherein:
R is H;
R$^1$ is hydrogen, alkyl, alkoxy, hydroxy, trifluoromethyl, trifluoromethoxy, F, Cl, Br, or I;
R$^2$ is hydrogen, alkyl, heteroaryl, alkoxy, hydroxy, F, Cl, Br, or I;

R$^3$ is hydrogen or alkyl;
R$^4$ is hydrogen or alkyl;
ring A is optionally substituted heterocycloamino;
Het is cycloalkylaminoalkyl, cycloalkylalkylaminoalkyl, heteroaryl, heterocycle, heterocyclylcarbonylalkyl, heterocyclylalkylcarbonyl, or heterocyclylalkyl;
X is OR$_8$ (wherein R$_8$ is hydrogen or alkyl) or NR$_8$R$_9$, wherein R$^8$ and R$^9$ are independently hydrogen or alkyl; or R$^8$ and R$^9$ together with the nitrogen atom to which they are attached form a heterocycloamino ring; and
n is 0 or 1; or
a pharmaceutically acceptable salt thereof.

In yet another aspect this invention is directed to a pharmaceutical composition comprising one or more compound(s) of Formulas (I) or (IV) or a pharmaceutically acceptable salt thereof and a pharmaceutically acceptable excipient.

In another aspect, this invention is directed to a method of treating diseases mediated by abnormal protein kinase (PK) activity, in particular, receptor tyrosine kinases (RTKs), non-receptor protein tyrosine kinases (CTKs) and serine/threonine protein kinases (STKs), in an organism, in particular humans, which method comprises administering to said organism a pharmaceutical composition comprising a compounds of Formulas (I) or (IV) and a pharmaceutically acceptable excipient. Specifically, the diseases mediated by EGF, Met, HER2, HER3, HER4, IR, IGF-1R, IRR, PDGFRα, PDGFRβ, CSFIR, C-Kit, C-fms, Flk-1R, Flk4, KDR/Flk-1, Flt-1, flt-3, FGFR-1R, FGFR-2R, FGFR-3R, FGFR-4R, Src, Frk, Btk, Csk, Abl, ZAP70, Fes/Fps, Fak, Jak, Ack, Yes, Fyn, Lyn, Lck, Blk, Hck, Fgr, Yrk, CDK2 and Raf. In particular diseases mediated by VEGFR, c-kit, and/or PDGFR kinases. Such diseases include by way of example and not limitation, cancers such as lung cancer, NSCLC (non small cell lung cancer), bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, brain stem gliomas or pituitary adenomas), Barrett's esophagus (pre-malignant syndrome), neoplastic cutaneous disease, psoriasis, mycoses fungoides, and benign prostatic hypertrophy, diabetes related diseases such as diabetic retinopathy, retinal ischemia, and retinal neovascularization, hepatic cirrhosis, cardiovascular disease such as atherosclerosis, immunological disease such as autoimmune disease and renal disease. Preferably, the disease is cancer such as acute myeloid leukemia, colorectal cancer, melanoma, glioblastoma, and non-small cell lung carcinoma.

The above method can also be carried out in combination with a chemotherapeutic agent. In one embodiment, the chemotherapeutic agent is selected from the group consisting of mitotic inhibitors, alkylating agents, anti-metabolites, cell cycle inhibitors, enzymes, topoisomerase inhibitors, biological response modifiers, anti-hormones, antiangiogenic agents such as MMP-2, MMP-9 and COX-2 inhibitors, and anti-androgens.

Examples of useful COX-II inhibitors include Vioxx™, CELEBREX™ (alecoxib), valdecoxib, rofecoxib, and Cox 189. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606, 046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[(4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds.

Other anti-angiogenesis agents, including other COX-II inhibitors and other MMP inhibitors, can also be used in the present invention.

Compounds of Formulas (I) or (IV) can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN.TM. (Genentech, Inc. of South San Francisco, Calif., USA). EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein.

EGFR-inhibiting agents include, but are not limited to, the monoclonal antibodies C225 and anti-EGFR 22 Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

These and other EGFR-inhibiting agents can be used in the present invention. VEGF inhibitors, for example SU-5416, SU 11248, SU-6668 (Sugen Inc. of South San Francisco, Calif., USA), can also be combined with a compounds of Formulas (I) or (IV). VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 01/60814, WO 98/50356 (published Nov. 12, 1998), U.S. Pat. No. 5,883, 113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with a compounds of Formulas (I) or (IV) for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. The erbB2 receptor inhibitor compounds and substance described in the aforementioned PCT applications and U.S. patents, as well as other compounds and substances that inhibit the erbB2 receptor, can be used with compounds of Formulas (I) or (IV), in accordance with the present invention.

Compounds of Formulas (I) or (IV) can also be used with other agents useful in treating cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors, for example the farnesyl protein transferase inhibitors described in the references cited in the "Background" section, of U.S. Pat. No. 6,258,824 B1. Specific CTLA4 antibodies that can be used in the present invention include those described in U.S. Provisional Application No. 60/113,647 (filed Dec. 23, 1998) which is incorporated by reference in its entirety, however other CTLA4 antibodies can be used in the present invention.

The above method can be also be carried out in combination with radiation therapy, wherein the amount of compounds of Formulas (I) or (IV) in combination with the radiation therapy effective in treating the above diseases.

Techniques for administering radiation therapy are known in the art, and these techniques can be used in the combination therapy described herein. The administration of the compound of the invention in this combination therapy can be determined as described herein.

In another aspect, this invention is directed to a method of modulating the catalytic activity (e.g., inhibiting the catalytic activity) of PKs, in particular receptor tyrosine kinases (RTKs), non-receptor protein tyrosine kinases (CTKs) and serine/threonine protein kinases (STKs), using a compound of this invention or a pharmaceutical composition comprising a compound of this invention and a pharmaceutically acceptable excipient. The method may be carried out in vitro or in vivo. In particular, the receptor protein kinase whose catalytic activity is modulated by a compound of this invention is selected from the group consisting of Met, EGF, HER2, HER3, HER4, IR, IGF-1R, IRR, PDGFRα, PDGFRβ, CSFIR, C-Kit, C-fms, Flk4, VEGFR, Flt-1, FGFR-1R, FGFR-2R, FGFR-3R and FGFR-4R, in particular VEGFR and/or PDGFR kinases. The cellular tyrosine kinase whose catalytic activity is modulated by a compound of this invention is selected from the group consisting of Src, Frk, Btk, Csk, Abl, ZAP70, Fes/Fps, Fak, Jak, Ack, Yes, Fyn, Lyn, Lck, Blk, Hck, Fgr and Yrk. The serine-threonine protein kinase whose catalytic activity is modulated by a compound of this invention is selected from the group consisting of CDK2 and Raf.

In yet another aspect, this invention is directed to the use of compounds of Formulas (I) or (IV) in the preparation of a medicament which is useful in the treatment of a disease mediated by abnormal VEGFR and/or PDGFR kinase activity.

In another aspect, this invention is directed intermediates of Formula (II):

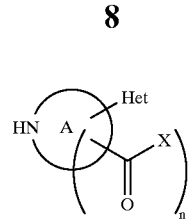

(II)

where Het and A are as defined above. Compounds of formula (II) are useful in the synthesis of compounds of Formula (I) disclosed above.

In another aspect, this invention is directed intermediates of Formula (V):

(V)

where Het, A, X and n are as defined above. Compounds of formula (V) are useful in the synthesis of compounds of Formula (IV) disclosed above.

In another aspect, this invention is directed to a method of preparing a compound of Formula (I) or (IV) which method comprises reacting a compound of formula (III) below:

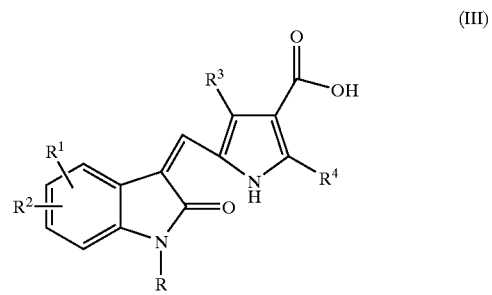

(III)

where R is hydrogen and $R^1$–$R^5$ are as defined in compounds of Formula (I), with a compound of Formula (II) shown above, in the presence of a coupling agent;
  (i) optionally modifying any of the R—$R^5$ groups; and
  (ii) optionally preparing an acid addition salt; and
  (iii) optionally preparing a free base.

Lastly, this invention is also directed to a method of identifying a chemical compound that modulates the catalytic activity of a protein kinase utilizing a compound of Formula (I) or (IV) as a reference which method comprises by contacting cells expressing said protein kinase with said compound or a compound of Formula (I) and then monitoring said cells for an effect.

DETAILED DESCRIPTION OF THE INVENTION

Definitions

Unless otherwise stated the following terms used in the specification and claims have the meanings discussed below:

"Alkyl" refers to a saturated straight or branched hydrocarbon radical of one to six carbon atoms, preferably one to four carbon atoms e.g., methyl, ethyl, propyl, 2-propyl, n-butyl, iso-butyl, tert-butyl, pentyl, hexyl, and the like, preferably methyl, ethyl, propyl, or 2-propyl.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like, preferably methylene, ethylene, or propylene.

"Cycloalkyl" refers to a saturated cyclic hydrocarbon radical of three to six carbon atoms e.g., cyclopropyl, cyclobutyl, cyclopentyl or cyclohexyl.

"Alkoxy" means a radical —OR where R is an alkyl as defined above e.g., methoxy, ethoxy, propoxy, butoxy, and the like.

"Alkoxycarbonyl" means a radical —COOR where R is an alkyl as defined above e.g., methoxycarbonyl, ethoxycarbonyl, propoxycarbonyl, butoxycarbonyl, and the like.

"Alkylthio" means a radical —SR where R is an alkyl as defined above e.g., methylthio, ethylthio, propylthio, butylthio, and the like.

"Alkylamino" and "dialkylamino" means a radical —NHR and —NRR' respectively, where R and R' independently represent an alkyl group as defined herein. Representative examples include, but are not limited to methylamino, ethylamino, propylamino, dimethylamino, methylethylamino, di-(1-methylethyl)-amino, and the like.

"Cycloalkylalkyl" means a saturated straight or branched monovalent hydrocarbon radical of one to six carbon atoms substituted with one or two cycloalkyl group as defined above e.g., cyclopropylmethyl, cyclopropylethyl, cyclobutylmethyl, cyclohexylethyl, and the like.

"Cycloalkylamino" means a —NRR' group where R is hydrogen or alkyl and R' is cycloalkyl e.g., cyclopropylamino, cyclobutylamino, cyclohexylamino, and the like.

"Cycloalkylaminoalkyl" means a -(alkylene)-NRR' group where R is hydrogen or alkyl and R' is cycloalkyl e.g., cyclopropylaminomethyl, cyclopropylaminoethyl, cyclobutylaminomethyl, cyclohexylaminoethyl, and the like.

"Cycloalkylalkylaminoalkyl" means a -(alkylene)-NRR' group where R is hydrogen or alkyl and R' is cycloalkylalkyl as defined above e.g., cyclopropylmethylaminomethyl, cyclopropylmethylaminoethyl, cyclobutylmethylaminomethyl, cyclohexylmethylaminoethyl, and the like.

"Alkylaminocarbonyl" and "dialkylaminocarbonyl" means a radical —CONHR and —CONRR' respectively, where R and R' independently represent an alkyl group as defined herein. Representative examples include, but are not limited to methylaminocarbonyl, ethylaminocarbonyl, propylaminocarbonyl, dimethylaminocarbonyl, methylethylaminocarbonyl, di(1-methylethyl)aminocarbonyl, and the like.

"Halo" means fluoro, chloro, bromo, or iodo, preferably fluoro and chloro.

"Haloalkyl" means alkyl substituted with one or more, preferably one, two or three, same or different halo atoms, e.g., —CH$_2$Cl, —CF$_3$, —CH$_2$CF$_3$, —CH$_2$CCl$_3$, and the like.

"Haloalkoxy" means a radical —OR where R is an haloalkyl as defined above e.g., trifluoromethoxy, trichloroethoxy, 2,2-dichloropropoxy, and the like.

"Hydroxyalkyl" means a saturated straight or branched monovalent hydrocarbon radical of one to six carbon atoms substituted with one or two hydroxy groups, provided that if two hydroxy groups are present they are not both on the same carbon atom. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl,2,3-dihydroxypropyl, and 1-(hydroxymethyl)-2-hydroxyethyl.

"Alkoxyalkyl" means a saturated straight or branched monovalent hydrocarbon radical of one to six carbon atoms substituted with one or two alkoxy groups as defined above, e.g., methoxymethyl, 2-methoxyethyl, 2-methoxypropyl, 3-methoxypropyl, ethoxymethyl, 2-ethoxyethyl, and the like.

"Aminoalkyl" means a saturated straight or branched monovalent hydrocarbon radical of one to six carbon atoms substituted with one or two —NH$_2$ e.g., 2-aminoethyl, 3-aminopropyl, 2-aminopropyl, 2-, 3-, or 4-aminobutyl, and the like.

"Aminoalkylcarbonyl" means a radical 'COR where R is an aminoalkyl group as defined above e.g., 2-aminoethylcarbonyl, 3-aminopropylcarbonyl, 2-aminopropylcarbonyl, 2-, 3-, or 4-aminobutylcarbonyl, and the like.

"Alkylaminoalkyl" means a saturated straight or branched monovalent hydrocarbon radical of one to six carbon atoms substituted with one or two —NHR where R is alkyl, or acyl, e.g., 2-N-methylaminoethyl, 2-N-ethylaminoethyl, 2-N-acetylaminoethyl, and the like.

"Alkylaminoalkylcarbonyl" means a radical —COR where R is an alkylaminoalkyl group as defined above e.g., 2-N-methylaminoethylcarbonyl, 2-N-ethylaminoethylcarbonyl, 2-N-acetylaminoethylcarbonyl, and the like.

"Dialkylaminoalkyl" means a saturated straight or branched monovalent hydrocarbon radical of one to six carbon atoms substituted with one or two —NRR' where R and R' are independently selected from alkyl, e.g., 2-N,N-diethylaminoethyl, 2-N,N-diethylaminopropyl, and the like.

"Dialkylaminoalkylcarbonyl" means a radical —COR where R is an dialkylaminoalkyl group as defined above e.g., 2-N,N-diethylaminoethylcarbonyl, 2-N,N-diethylaminopropyl-carbonyl, and the like.

"Acyl" means a radical —C(O)R where R is hydrogen, alkyl, or haloalkyl as defined herein, e.g., formyl, acetyl, trifluoroacetyl, butanoyl, and the like.

"Aryl" refers to a monocyclic or fused aromatic ring (i.e., rings which share an adjacent pair of atoms) group of 6 to 12 carbon atoms e.g., phenyl, napthyl, and the like. The aryl group may be substituted or unsubstituted. When substituted, the aryl group is substituted with one or more, more preferably one, two or three, even more preferably one or two substituents independently selected from the group consisting of alkyl, haloalkyl, alkylthio, halo, hydroxy, alkoxy, acyl, nitro, haloalkoxy, carboxy, alkoxycarbonyl, amino, alkylamino or dialkylamino.

"Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, triazole, tetrazole, triazine, and carbazole. The heteroaryl group may be substituted or unsubstituted. When substituted, the heteroaryl group is substituted with one or more, more preferably one, two or three, even more preferably one or two substituents independently selected from the group consisting of alkyl, haloalkyl, halo, hydroxy, alkoxy, acyl, nitro, haloalkoxy, carboxy, alkoxycarbonyl, amino, alkylamino or dialkylamino.

"Heterocycle" or "heterocyclyl" means a saturated or unsaturated cyclic radical of 3 to 8 ring atoms in which one, two or three ring atoms are heteroatoms selected from N, O, or S(O)$_n$ (where n is an integer from 0 to 2), the remaining ring atoms being C, where one or two C atoms may optionally be replaced by a carbonyl group. Preferably, the heterocyle ring contains at least one nitrogen atom in the ring. When unsaturated, the heterocyle contains one or two double bonds provided that the ring is not aromatic. The heterocyclyl ring may be optionally substituted independently with one or more, preferably one, two, or three substituents selected from alkyl (wherein the alkyl may be optionally substituted with one or two substituents independently selected from carboxy or —COOR where R is alkyl), haloalkyl, halo, nitro, cyano, hydroxy, alkoxy, amino, alkylamino, dialkylamino, hydroxyalkyl, carboxyalkyl, aminoalkyl, alkylaminoalkyl, dialkylaminoalkyl, aminoalkylcarbonyl, alkylaminocarbonyl, dialkylaminocarbonyl, alkoxyalkyl, alkylaminoalkylcarbonyl, dialkylaminoalkylcarbonyl, aryl, heteroaryl, aryloxy, aralkyl, heteroaralkyl, and —COR (where R is alkyl). More specifically the term heterocyclyl includes, but is not limited to, tetrahydropyranyl, 2,2-dimethyl-1,3-dioxolane, piperidino, N-methylpiperidin-3-yl, piperazino, N-methylpyrrolidin-3-yl, pyrrolidino, morpholino, thiomorpholino, thiomorpholino-1-oxide, thiomorpholino-1,1-dioxide, 4-ethyloxycarbonylpiperazino, 3-oxopiperazino, 2-imidazolidone, 2-pyrrolidinone, 2-oxohomopiperazino, tetrahydropyrimidin-2-one, and the derivatives thereof.

"Heterocycloamino" means a saturated cyclic radical of 3 to 8 ring atoms in which at least one of the ring atoms is nitrogen and optionally where one or two additionally ring atoms are heteroatoms selected from —NR$^a$— (where R$^a$ is alkyl, substituted alkyl acyl, aryl, or heteroaryl), O, or S(O)$_n$ (where n is an integer from 0 to 2), the remaining ring atoms being C, where one or two C atoms may optionally be replaced by a carbonyl group. The heterocycloamino ring may be optionally substituted independently with one, two, or three substituents selected from alkyl, hydroxyalkyl, or carboxy. More specifically the term heterocycloamino includes, but is not limited to, piperidin-1-yl, piperazin-1-yl, pyrrolidin-1-yl, 2-oxo-pyrrolidin-1-yl, 2,5-dioxo-pyrrolidin-1-yl, morpholin-4-yl, thiomorpholin-4-yl, thiomorpholino-1-oxide, thiomorpholino-1,1-dioxide, 4-ethyloxycarbonylpiperazin-1-yl, 3-oxopiperazin-1-yl, 2-imidazolidon-1-yl, 2-pyrrolidinon-1-yl, 2-oxohomopiperazino, tetrahydropyrimidin-2-one, and the derivatives thereof. The heterocycloamino group is a subset of the heterocycle group defined above.

"Optionally substituted heterocycloamino" means a non-aromatic cyclic radical of 4 to 8 ring atoms containing one or two double bonds within the ring provided that the ring is not aromatic, and in which at least one of the ring atoms is nitrogen and optionally where one or two additionally ring atoms are heteroatoms independently selected from —NR$^a$— (where R$^a$ is alkyl, substituted alkyl acyl, aryl, or heteroaryl), O, or S(O)$_n$ (where n is an integer from 0 to 2), the remaining ring atoms being C. One or two C ring atoms may optionally be replaced by a carbonyl group. The heterocycloamino ring may be optionally substituted independently with one, two, or three substituents selected from alkyl, cycloalkylalkyl, halo, nitro, cyano, hydroxy, alkoxy, amino, alkylamino, and dialkylamino.

"Hydroxy" refers to an —OH group.

"Aryloxy" refers to both an —OR where R is an aryl group, as defined herein. Representative examples include, but are not limited to, phenyloxy, F, Cl, or Brphenyloxy, and the like, and derivatives thereof.

"Cyano" refers to a —C≡N group.

"Nitro" refers to a —NO$_2$ group.

"Aralkyl" means alkyl as defined above which is substituted with an aryl group as defined above, e.g.,
—CH$_2$phenyl, —(CH$_2$)$_2$phenyl, —(CH$_2$)$_3$phenyl, —H$_2$CH(CH$_3$)CH$_2$phenyl, and the like and derivatives thereof.

"Heteroaralkyl" group means alkyl as defined above which is substituted with a heteroaryl group, e.g., —CH$_2$pyridinyl, —(CH$_2$)$_2$pyrimidinyl, —(CH$_2$)$_3$imidazolyl, and the like, and derivatives thereof.

"Heterocyclylalkyl" group means alkyl as defined above which is substituted with a heterocycle group, e.g., —CH$_2$pyrrolidin-1-yl, —(CH$_2$)$_2$piperidin-1-yl, and the like, and derivatives thereof.

"Heterocyclylcarbonylalkyl" group means -(alkylene)-C(O)-heterocyclyl, e.g., 2-morpholine-4-ylacetyl.

"Heterocyclylalkylcarbonyl" group means —C(O)-(alkylene)-heterocyclyl, e.g., 2-morpholin-4-yl-2-oxoethyl.

"Optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocyclo group is not substituted with the alkyl group.

The terms "2-indolinone", "indolin-2-one" and "2-oxindole" are used interchangeably herein to refer to a molecule having the chemical structure:

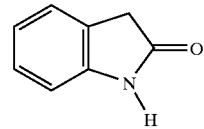

The term "pyrrole" refers to a molecule having the chemical structure:

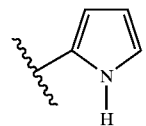

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. For example, if the a substituent in a compound of Formula (I) or (IV) is 2-hydroxyethyl, then the carbon to which the hydroxy group is attached is an asymmetric center and therefore the compound of Formula (I) or (IV) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

The compounds of Formula (I) or (IV) may exhibit the phenomena of tautomerism and structural isomerism. For example, the compounds described herein may adopt an E or a Z configuration about the double bond connecting the 2-indolinone moiety to the pyrrole moiety or they may be a mixture of E and Z. This invention encompasses any tautomeric or structural isomeric form and mixtures thereof which possess the ability to modulate RTK, CTK and/or STK activity. Preferably, the compounds of Formula (I) or (IV) have a Z configuration about the double bond connecting the 2-indolinone moiety to the pyrrole moiety.

It is contemplated that a compound of Formula (I) or (IV) would be metabolized by enzymes in the body of the organism such as human being to generate a metabolite that can modulate the activity of the protein kinases. Such metabolites are within the scope of the present invention.

A "pharmaceutical composition" refers to a mixture of one or more of the compounds described herein, or pharmaceutically acceptable salts or prodrugs thereof, with other chemical components, such as pharmaceutically acceptable excipients. The purpose of a pharmaceutical composition is to facilitate administration of a compound to an organism.

"Pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Pharmaceutically acceptable salt" refers to those salts which retain the biological effectiveness and properties of the parent compound. Such salts include:

(1) acid addition salt which is obtained by reaction of the free base of the parent compound with inorganic acids such as hydrochloric acid, hydrobromic acid, nitric acid, phosphoric acid, sulfuric acid, and perhcloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The compound of Formula (I) or (IV) may also act as a prodrug. A "prodrug" refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention that is administered as an ester (the "prodrug"), carbamate or urea. For example, a compound of Formula (I) or (IV) where R is —$COR^6$ or —$PO(OR^5)_2$ hydrolyzes in vivo to generate a corresponding compound of Formula (I) or (IV) where R is hydrogen.

"PK" refers to receptor protein tyrosine kinase (RTKs), non-receptor or "cellular" tyrosine kinase (CTKs) and serine-threonine kinases (STKs).

"Method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

"Modulation" or "modulating" refers to the alteration of the catalytic activity of RTKs, CTKs and STKs. In particular, modulating refers to the activation of the catalytic activity of RTKs, CTKs and STKs, preferably the activation or inhibition of the catalytic activity of RTKs, CTKs and STKs, depending on the concentration of the compound or salt to which the RTK, CTK or STK is exposed or, more preferably, the inhibition of the catalytic activity of RTKs, CTKs and STKs.

"Catalytic activity" refers to the rate of phosphorylation of tyrosine under the influence, direct or indirect, of RTKs and/or CTKs or the phosphorylation of serine and threonine under the influence, direct or indirect, of STKs.

"Contacting" refers to bringing a compound of this invention and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished "in vitro," i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, i.e., the $IC_{50}$ of the compound, defined below, can be determined before use of the compounds in vivo with more complex living organisms is attempted. For cells outside the organism, multiple methods exist, and are well-known to those skilled in the art, to get the PKs in contact with the compounds including, but not limited to, direct cell microinjection and numerous transmembrane carrier techniques.

"In vitro" refers to procedures performed in an artificial environment such as, e.g., without limitation, in a test tube or culture medium.

"In vivo" refers to procedures performed within a living organism such as, without limitation, a mouse, rat or rabbit.

"PK related disorder," "PK driven disorder," and "abnormal PK activity" all refer to a condition characterized by inappropriate, i.e., under or, more commonly, over, PK catalytic activity, where the particular PK can be an RTK, a CTK or an STK. Inappropriate catalytic activity can arise as the result of either: (1) PK expression in cells which normally do not express PKs, (2) increased PK expression leading to unwanted cell proliferation, differentiation and/or growth, or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, of course, the converse, wherein the severity of one or more symptoms of a cellular disorder increase as the level of the PK activity decreases.

"Treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

"Organism" refers to any living entity comprised of at least one cell. A living organism can be as simple as, for example, a single eukariotic cell or as complex as a mammal, including a human being.

"Therapeutically effective amount" refers to that amount of the compound being administered which will relieve to some extent one or more of the symptoms of the disorder being treated. In reference to the treatment of cancer, a therapeutically effective amount refers to that amount which has the effect of:

(1) reducing the size of the tumor;
(2) inhibiting (that is, slowing to some extent, preferably stopping) tumor metastasis;
(3) inhibiting to some extent (that is, slowing to some extent, preferably stopping) tumor growth, and/or,
(4) relieving to some extent (or, preferably, eliminating) one or more symptoms associated with the cancer.

"Monitoring" means observing or detecting the effect of contacting a compound with a cell expressing a particular PK. The observed or detected effect can be a change in cell phenotype, in the catalytic activity of a PK or a change in the interaction of a PK with a natural binding partner. Techniques for observing or detecting such effects are well-known in the art.

The above-referenced effect is selected from a change or an absence of change in a cell phenotype, a change or absence of change in the catalytic activity of said protein kinase or a change or absence of change in the interaction of said protein kinase with a natural binding partner in a final aspect of this invention.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

"Natural binding partner" refers to a polypeptide that binds to a particular PK in a cell. Natural binding partners can play a role in propagating a signal in a PK-mediated signal transduction process. A change in the interaction of the natural binding partner with the PK can manifest itself as an increased or decreased concentration of the PK/natural binding partner complex and, as a result, in an observable change in the ability of the PK to mediate signal transduction.

PREFERRED EMBODIMENTS

While the broadest definition is set forth in the Summary of the Invention, certain compounds of Formula (I) or (IV) set forth below are preferred.

a. One preferred group of compounds is that wherein:
$R^1$ is hydrogen, methyl, methoxy, hydroxy, F, Cl or Br. Preferably $R^1$ is hydrogen or F, more preferably F; and
$R^2$ is hydrogen, methyl, methoxy, hydroxy, F, Cl or Br. Preferably $R^1$ is hydrogen or F, more preferably hydrogen.

Within this group, a more preferred group of compounds is that wherein:
$R^1$ is at the 5-position of the indolinone ring; and
$R^2$ is hydrogen, —PO(OH)$_2$, —COCH$_3$, or pyrrolidin-1-ylmethyl, more preferably hydrogen.

Within the above preferred and more preferred groups, an even more preferred group of compounds is that wherein:
$R^3$ and $R^4$ are independently hydrogen or methyl, more preferably methyl.

Within the above preferred and more preferred and even more preferred groups, a particularly preferred group of compounds is that wherein:
A is a heterocycloamino group of 4 to 6 ring atoms, preferably azetidin-1-yl, pyrrolidin-1-yl, piperidin-1-yl, or piperazin-1-yl; more preferably pyrrolidin-1-yl; and
Het is either:
(i) a heterocycle containing 4 to 6 ring atoms wherein one or two ring atoms are selected from the group consisting of nitrogen, oxygen, or sulfur, the remaining ring atoms being carbon. The heterocycle ring may optionally substituted with one or two alkyl. Preferably, the heterocycle is piperdin-1-yl, morpholin-4-yl, thiomorpholin-4-yl, piperazin-1-yl, 2,6-dimethylmorpholin-4-yl, or 2,6-dimethylpiperazin-1-yl and is located at the 3 or 4-position of the A ring;
(ii) heteroaryl, preferably pyridine, or
(iii) heterocyclylalkyl wherein the heterocycle contains 4 to 6 ring atoms wherein one or two ring atoms are selected from the group consisting of nitrogen, oxygen, or sulfur, the remaining ring atoms being carbon. Preferably, the heterocycle is pyrrolidin-1-ylmethyl, pyrrolidin-1ylethyl, pyrrolidin-1-ylmethyl, or pyrrolidin-1ylethyl. Even more preferably, pyrrolidin-1-ylmethyl, pyrrolidin-1ylethyl, pyrrolidin-1-ylmethyl, or pyrrolidin-1ylethyl is attached to the C-2-position of the pyrrolidin-1-yl (the A ring above) and the stereochemistry at the C-2 position of said pyrroldin-1-yl ring (the A ring) is either R or S.

b. Another preferred group of compounds is that wherein:
Het is a heterocycle containing 4 to 6 ring atoms wherein one or two ring atoms are selected from the group consisting of nitrogen, oxygen, or sulfur, the remaining ring atoms being carbon. The heterocyle ring may optionally substituted with one or two alkyl. Preferably, the heterocycle is piperdin-1-yl, morpholin-4-yl, thiomorpholin-4-yl, piperazin-1-yl, 2,6-dimethylmorpholin-4-yl, or 2,6-dimethylpiperazin-1-yl and is located at the 3 or 4-position of the A ring.

Within this group, a more preferred group of compounds is that wherein A is a heterocycloamino group of 4 to 6 ring atoms, preferably azetidin-1-yl, pyrrolidin-1-yl, piperidin-1-yl, or piperazin-1-yl.

Within this group, a more preferred group of compounds is that wherein:
R is hydrogen;
$R^1$ is fluoro and is at the 5-position of the indolinone ring.
Representative compounds of this invention are shown in Table 1, below:

TABLE 1

| Cpd. # | | M.W. |
|---|---|---|
| 1 | | 434.5 |
| 2 | | 452.5 |
| 3 | | 469.0 |
| 4 | | 436.5 |
| 5 | | 495.6 |

TABLE 1-continued

| Cpd. # | | M.W. |
|---|---|---|
| 6 | | 424.5 |
| 7 | | 440.9 |
| 8 | | 452.5 |
| 9 | | 469.0 |
| 10 | | 436.53 |

TABLE 1-continued
| Cpd. # | | M.W. |
|---|---|---|
| 11 | 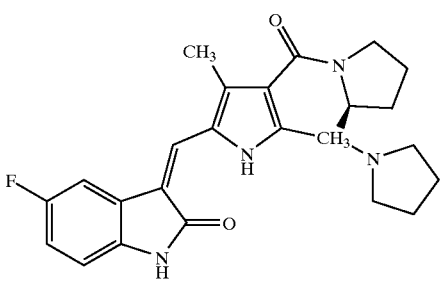 | 436.53 |
| 12 | 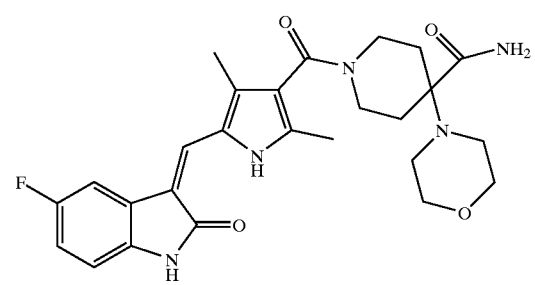 | 495.55 |
| 13 | 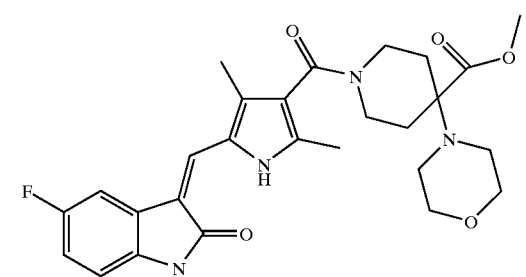 | 510.56 |
| 14 | 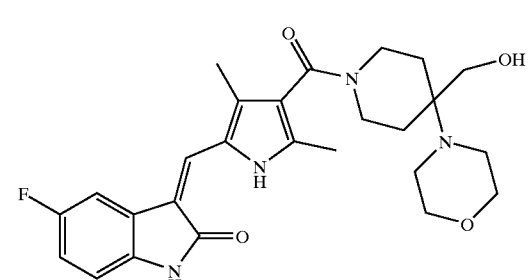 | 482.55 |
| 15 | 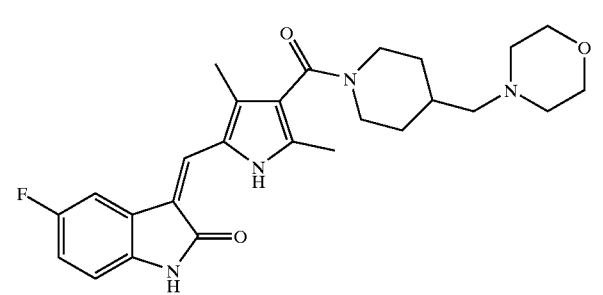 | 466.55 |

TABLE 1-continued
| Cpd. # | | M.W. |
|---|---|---|
| 16 | 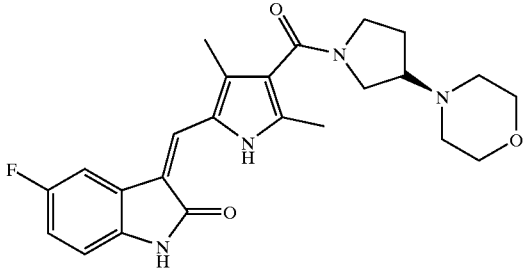 | 438.49 |
| 17 | 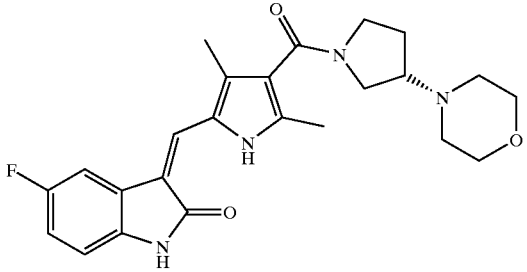 | 438.49 |
| 18 | 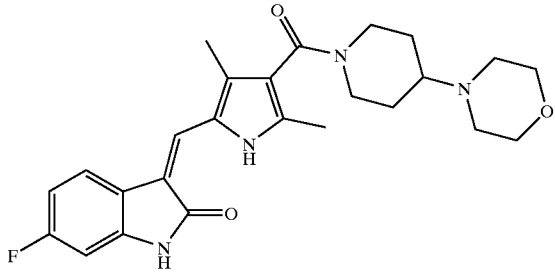 | 452.52 |
| 19 | 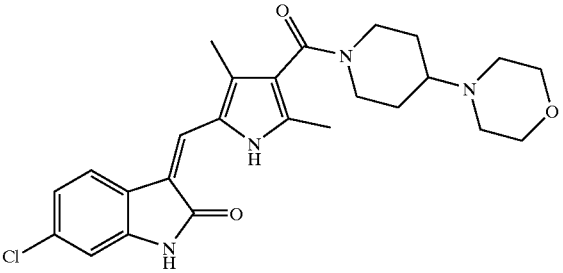 | 468.98 |
| 20 | 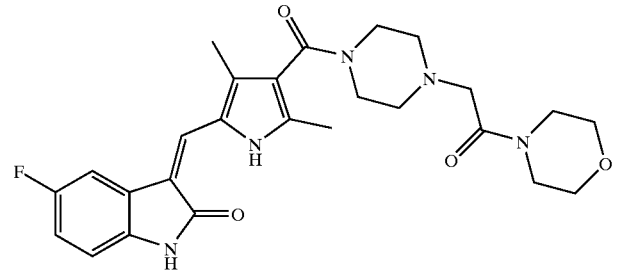 | 495.55 |

TABLE 1-continued

| Cpd. # | | M.W. |
|---|---|---|
| 21 | 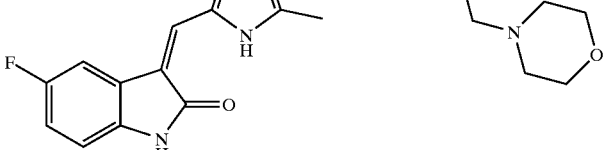 | 495.55 |
| 22 | 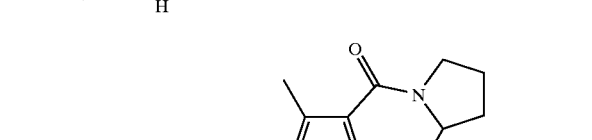 | 452.52 |
| 23 | 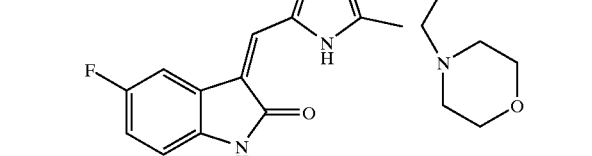 | 452.52 |
| 24 | 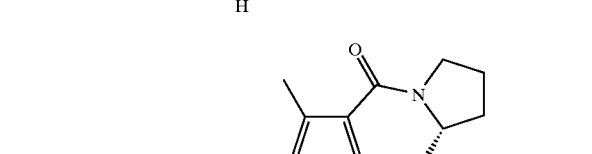 | 481.56 |
| 25 | 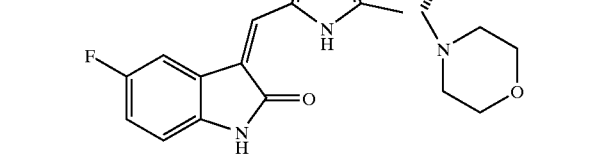 | 466.55 |

Utility

The compounds of Formula (I) or (IV) inhibit VEGFR, PDGFR and c-kit and are therefore useful in treating diseases mediated by abnormal VEGFR, PDGFR and/or c-kit activity. Such diseases include, and are not limited to, cancers such as such as T-cell lymphoma, acute lymphoblasitc leukemia, acute myeloid leukemia, melanoma, glioblastoma and others (see Bellamy W. T. et al., Cancer Res. 1999, 59, 728–733). In addition VEGFR also plays a role in ocular diseases such as diabetic retinopathy, retinal ischemia, and retinal neovascularization. Accordingly, the compounds of the present invention are also useful in the treatment of ocular diseases. It is further contemplated that the compunds of the present invention may inhibit other receptor tyrosine kinases (RTKs), non-receptor protein tyrosine kinases (CTKs) and serine/threonine protein kinases (STKs). Accordingly, these compounds would be useful in treatment of diseases mediated by these kinases such as cancer selected from the group consisting of squamous cell carcinoma, astrocytoma, Kaposi's sarcoma, glioblastoma, lung cancer, bladder cancer, head and neck cancer, melanoma, ovarian cancer, prostate cancer, breast cancer, non small-cell lung cancer, glioma, acute myeloid leukemia, colorectal cancer, genitourinary cancer and gastrointestinal cancer, diabetes, an autoimmune disorder, a hyperproliferation disorder, restenosis, fibrosis, psoriasis, von Hippel-Lindau disease, osteoarthritis, rheumatoid arthritis, angiogenesis, an inflammatory disorder, an immunological disorder and a cardiovascular disorder. Other diseases are disclosed in U.S. Pat. No. 5,792,783, the disclosure of which is incorporated herein by reference in its entirety.

Administration and Pharmaceutical Composition

A compound of the present invention or a pharmaceutically acceptable salt thereof, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

As used herein, "administer" or "administration" refers to the delivery of a compound of Formula (I) or (IV) or a pharmaceutically acceptable salt thereof or of a pharmaceutical composition containing a compound of Formula (I) or (IV) or a pharmaceutically acceptable salt thereof of this invention to an organism for the purpose of prevention or treatment of a PK-related disorder.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. The preferred routes of administration are oral and intravenous.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

Pharmaceutical compositions which may also be used include hard gelatin capsules. As a non-limiting example, the active compound capsule oral drug product formulation may be as 50 and 200 mg dose strengths. The two dose strengths are made from the same granules by filling into different size hard gelatin capsules, size 3 for the 50 mg capsule and size 0 for the 200 mg capsule. The composition of the formulation may be, for example, as indicated in Table 2.

TABLE 2

| Ingredient Name/Grade | Concentration in Granulation (% w/w) | Amount in 50 mg Capsule (mg) | Amount in 200 mg Capsule (mg) |
| --- | --- | --- | --- |
| Active Compound NF | 65.0 | 50.0 | 200.0 |
| Mannitol NF | 23.5 | 18.1 | 72.4 |
| Croscarmellose sodium NF | 6.0 | 4.6 | 18.4 |
| Povidone K 30 NF | 5.0 | 3.8 | 15.2 |

TABLE 2-continued

| Ingredient Name/Grade | Concentration in Granulation (% w/w) | Amount in 50 mg Capsule (mg) | Amount in 200 mg Capsule (mg) |
| --- | --- | --- | --- |
| Magnesium stearate NF | 0.5 | 0.38 | 1.52 |
| Capsule, Swedish yellow NF | | Size 3 | Size 0 |

The capsules may be packaged into brown glass or plastic bottles to protect the active compound from light. The containers containing the active compound capsule formulation must be stored at controlled room temperature (15–30° C.).

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the fomulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharamcologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of such a co-solvent system may be varied considerably without destroying its solubility and toxicity characteristics. Furthermore, the identity of the co-solvent components may be varied: for example, other low-toxicity nonpolar surfactants may be used instead of Polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the PK modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, malate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), Calcium hydroxide (Ca(OH)$_2$), etc.).

Pharmaceutical compositions suitable for use in the present invention include compositions wherein the active ingredients are contained in an amount sufficient to achieve the intended purpose, e.g., the modulation of PK activity or the treatment or prevention of a PK-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of the PK activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50–90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10–90% of the time, preferably between 30–90% and most preferably between 50–90%.

At present, the therapeutically effective amounts of compounds of Formula (I) or (IV) may range from approximately 25 mg/m$^2$ to 1500 mg/m$^2$ per day; preferably about 200 mg/m$^2$/day.

In cases of local administration or selective uptake, the effective local concentration of the drug may not be related to plasma concentration and other procedures known in the art may be employed to determine the correct dosage amount and interval.

The amount of a composition administered will, of course, be dependent on the subject being treated, the severity of the affliction, the manner of administration, the judgment of the prescribing physician, etc.

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

It is also an aspect of this invention that a compound described herein might be combined with other chemotherapeutic agents for the treatment of the diseases and disorders discussed above. For instance, a compound, salt or prodrug of this invention might be combined with alkylating agents such as fluorouracil (5-FU) alone or in further combination with leukovorin; or other alkylating agents such as, without limitation, other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

A compound of this invention can also be used in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

It is contemplated that a compound of this invention can also be used in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

In addition to the above, a compound of this invention could also be used in combination with the platinum coordination complexes (cisplatin, etc.); substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors such as anastrozole.

Finally, it is also contemplated that the combination of a compound of this invention will be effective in combination with Endostatin®, Gleevec®, Camptosar®, Herceptin®, Imclone C225, mitoxantrone or paclitaxel for the treatment of solid tumor cancers or leukemias such as, without limitation, acute myelogenous (non-lymphocytic) leukemia. The compounds of this invention can also be used with a COX-2 inhibitor.

For the combination therapies and pharmaceutical compositions described herein, the effective amounts of the compound of the invention and of the chemotherapeutic or other agent useful for inhibiting abnormal cell growth (e.g., other antiproliferative agent, anti-agiogenic, signal transduction inhibitor or immune-system enhancer) can be determined by those of ordinary skill in the art, based on the effective amounts for the compound described herein and those known or described for the chemotherapeutic or other agent. The formulations and routes of administration for such therapies and compositions can be based on the information described herein for compositions and therapies comprising the compound of the invention as the sole active agent and on information provided for the chemotherapeutic or other agent in combination therewith.

EXAMPLES

The following preparations and examples are given to enable those skilled in the art to more clearly understand and to practice the present invention. They should not be considered as limiting the scope of the invention, but merely as being illustrative and representative thereof.

Synthetic Examples

The Example numbers given below correspond to the compound numbers on Table 1.

Example 2

Synthesis of (3Z)-3-{[3,5-dimethyl-4-(morpholin-4-yl)piperidin-1-ylcarbonyl]-1H-pyrrol-2-ylmethylidene}-5-fluoro-1,3-dihydro-2H-indol-2-one

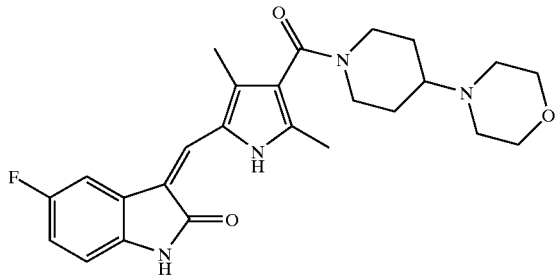

Step 1

To a stirred mixture of 4-amino-1-benzylpiperidine (Aldrich, 1.53 mL, 7.5 mmol), $K_2CO_3$ (2.28 g, 16.5 mmol), and dimethylformamide (DMF) (15 mL) heated at 50° C. was added dropwise over 60 min bis(2-bromoethyl) ether (Aldrich, tech. 90%, 0.962 mL, 7.65 mmol). After stirring 6 h at 80° C., TLC (90:10:1 chloroform/MeOH/aq. conc $NH_4OH$) indicated formation of a new spot. Heating was continued as the solvent was evaporated by blowing with a stream of nitrogen over 2 h. The crude material was relatively pure, but subjected to a relatively short silica gel column (1% to 6% gradient of 9:1 MeOH/aq. $NH_4OH$ in chloroform). Evaporation of the pure fractions gave ~1.7 g of the diamine 4-(morpholin-4-yl)-1-benzylpiperidine as a waxy solid.

$^1$HNMR (400 MHz, $d_6$-DMSO) δ7.31 (m, 4H), 7.26 (m 1H), 3.72 (t, J=4.7 Hz, 4H), 3.49 (s, 2H), 2.94 (br d, J=5.9 Hz, 2H), 2.54 (t, J=4.7 Hz, 4H), 2.19 (tt, J=11.5, 3.9 Hz, 1H), 1.96 (td, J=11.7, 2.2 Hz, 2H), 1.78 (br d, J=12.5 Hz, 2H), 1.55 (m, 2H).

Step 2

A stirred mixture of $Pd(OH)_2$ (20% on carbon (<50% wet), 390 mg, 25 wt %), methanol (50 mL), and ≦1.7 M HCl (3 eq, ~10.6 mL—including water added later when ppt was seen) under nitrogen was exchanged to 1 atm. hydrogen atmosphere by flushing (~20 sec) using a balloon of nitrogen into the vessel and out through an oil bubbler. After 20 min. the reaction mixture under hydrogen was heated to 50° C. and 4-(morpholin-4-yl)-1-benzylpiperidine (1.56 g, 6.0 mmol) in methanol (8 mL) was added dropwise over 30 min. After 10 h, tlc indicated all starting amine was consumed to a more polar spot (ninhydrin active). The reaction mixture was then filtered through Celite and evaporated to yield the 4-(morpholin-4-yl)piperidine dihydrochloride as an off-white solid. This material was subjected to free-basing using excess basic resin (>16 g, Bio-Rad Laboratories, AG 1-X8, 20–50 mesh, hydroxide form, methanol washed two times) and a methanol mixture of the amine hydrochloride. After swirling with the resin for 30 min., the methanol solution was decanted and evaporated to yield 932 mg of 4-(morpholin-4-yl)piperidine free base as a waxy crystalline solid.

$^1$HNMR (400 MHz, $d_6$-DMSO) δ3.53 (br s, 4H), 3.30 (v br s, 1H(+$H_2O$)), 2.92 (br d, J=11.7 Hz, 1H), 2.41 (s, 4H), 2.35 (~obscd t, J=11.7 Hz, 2H), 2.12 (br t, 1H), 1.65 (br d, J=11.7 Hz, 2H), 1.18 (br q, J=10.9 Hz, 2H); LCMS-APCI m/z 171 [M+1]$^+$.

Step 3

(3Z)-3-(3,5-Dimethyl-4-carboxy-1H-pyrrol-2-ylmethylidene)-5-fluoro-1,3-dihydro-2H-indol-2-one (120 mg, 0.40 mmol), prepared as described in published PCT Application WO01/60814, and BOP (221 mg, 0.50 mmol) were suspended in DMF (5 mL) with good stirring at room temperature and triethylamine (134 μL, 0.96 mmol) was added. After 10–15 min., to the homogeneous reaction mixture was added the 4-(morpholin-4-yl)piperidine (85 mg, 0.50 mmol) all at once. The reaction mixture was stirred for 48 h (might be done much earlier), then transferred to a funnel containing chloroform-isopropanol (5/1) and 5% aq. LiCl. The cloudy-orange organic phase was separated, washed with additional 5% aq LiCl (2×), 1 M aq NaOH (3×), satd aq NaCl (1×), and then dried ($Na_2SO_4$) and evaporated to yield the crude product (96.3% pure; trace hexamethylphosphoramide (HMPA) by $^1$HNMR). This crude product was then further purified by passage through a very short column (3 cm) of silica gel (5 to 15% gradient of MeOH in dichloromethane (DCM)) where a trace of faster moving 3E-isomer was removed. The pure fractions were evaporated and recrystallized overnight from a satd EtOAc soln which was diluted with $Et_2O$ (~3-fold) and chilled at 0° C. The mother liquor was decanted to yield after full vacuum the desired compound as orange crystals (153 mg 85%).

$^1$HNMR (400 MHz, $d_6$-DMSO) δ13.60 (s, 1H), 10.87 (s, 1H), 7.72 (dd, J=9.4, 2.7 Hz, 1H), 7.68 (s, 1H), 6.91 (td, J=9.3, 2.6 Hz, 1H), 6.82 (dd, J=8.6, 4.7 Hz, 1H), 3.54 (app br t, J=4.3 Hz, 4H), 3.31 (2×s, 3H+3H), 2.43 (br s, 4H), 2.36 (m, 1H), 2.25 (br m, 6H), 1.79 (br s, 2H), 1.22 (br s, 2H); LCMS m/z 453 [M+1]⁺.

Example 1

Proceeding as described in Example 2 above but substituting (3Z)-3-(3,5-dimethyl-4-carboxy-1H-pyrrol-2-ylmethylidene)-1,3-dihydro-2H-indol-2-one for (3Z)-3-(3,5-dimethyl-4-carboxy-1H-pyrrol-2-ylmethylidene)-5-fluoro-1,3-dihydro-2H-indol-2-one gave (3Z)-3-{[3,5-dimethyl-4-(morpholin-4-yl)piperidin-1-ylcarbonyl]-1H-pyrrol-2-ylmethylidene}-1,3-dihydro-2H-indol-2-one.

¹HNMR (400 MHz, d₆-DMSO) δ13.55 (s, 1H), 10.87 (s, 1H), 7.74 (d, J=7.6 Hz, 1H), 7.59 (s, 1H), 7.11 (t, J=7.6 Hz, 1H), 6.97 (t, J=7.6 Hz, 1H), 6.86 (d, J=7.4 Hz, 1H), 3.54 (app br t, J=4.3 Hz, 4H), 3.31 (2×s, 3H+3H), 2.43 (br s, 4H), 2.35 (m, 1H), 2.28 (br m, 6H), 1.79 (br s, 2H), 1.22 (br s, 2H); LCMS m/z 435 [M+1]⁺.

Example 3

Proceeding as described in Example 2 above but substituting (3Z)-3-(3,5-dimethyl-4-carboxy-1H-pyrrol-2-ylmethylidene)-5-chloro-1,3-dihydro-2H-indol-2-one for (3Z)-3-(3,5-dimethyl-4-carboxy-1H-pyrrol-2-ylmethylidene)-5-fluoro-1,3-dihydro-2H-indol-2-one gave (3Z)-3-{[3,5-dimethyl-4-(morpholin-4-yl)piperidin-1-ylcarbonyl]-1H-pyrrol-2-ylmethylidene}-5-chloro-1,3-dihydro-2H-indol-2-one.

¹HNMR (400 MHz, d₆-DMSO) δ13.56 (s, 1H), 10.97 (s, 1H), 7.95 (d, J=2.0 Hz, 1H), 7.74 (s, 1H), 7.11 (dd, J=8.2, 2.0 Hz, 1H), 6.85 (d, J=8.2 Hz, 1H), 3.54 (app br t, J=~4 Hz, 4H), 3.31 (2×s, 3H+3H), 2.43 (br s, 4H), 2.37 (m, 1H), 2.25 (br, m 6H), 1.79 (br s, 2H), 1.23 (br s, 2H); LCMS m/z 470 [M+1]⁺.

Example 4

Proceeding as described in Example 2 above but substituting 4-(morpholin-4-yl)-piperidine with commercially available 4-(1-pyrrolidinyl)-piperidine gave (3Z)-3-[3,5-dimethyl-4-[4-(pyrrolidin-1-yl)piperidin-1-ylcarbonyl]-1H-pyrrol-2-yl)methylidene]-5-fluoro-1,3-dihydro-2H-indol-2-one.

¹HNMR (400 MHz, d⁶-DMSO) E/Z isomer mixture; LCMS m/z 437 [M+1]⁺.

Example 18

Proceeding as described in Example 2 above but substituting (3Z)-3-(3,5-dimethyl-4-carboxy-1H-pyrrol-2-ylmethylidene)-5-fluoro-1,3-dihydro-2H-indol-2-one for (3Z)-3-(3,5-dimethyl-4-carboxy-1H-pyrrol-2-ylmethylidene)-6-fluoro-1,3-dihydro-2H-indol-2-one gave (3Z)-3-{[3,5-dimethyl-4-(morpholin-4-yl)piperidin-1-ylcarbonyl]-1H-pyrrol-2-ylmethylidene}-6-fluoro-1,3-dihydro-2H-indol-2-one.

¹HNMR (400 MHz, d₆-DMSO) δ13.41 (s, 1H), 11.02 (s, 1H), 7.79 (dd, J=8.2, 5.5 Hz, 1H), 7.60 (s, 1H), 6.81 (ddd, J=~11, 8.6, 2.5 Hz, 1H), 6.70 (dd, J=9.0, 2.3 Hz, 1H), 3.56 (app br t, J=~4 Hz, 4H), 2.45 (br s, 4H), 2.37 (m, 1H), 2.26 (br m, 6H), 1.81 (br s, 2H), 1.25 (br s, 2H); LCMS m/z 453 [M+1]⁺.

Example 19

Proceeding as described in Example 2 above but substituting (3Z)-3-(3,5-dimethyl-4-carboxy-1H-pyrrol-2-ylmethylidene)-6-chloro-1,3-dihydro-2H-indol-2-one for (3Z)-3-(3,5-dimethyl-4-carboxy-1H-pyrrol-2-ylmethylidene)-5-fluoro-1,3-dihydro-2H-indol-2-one gave (3Z)-3-{[3,5-dimethyl-4-(morpholin-4-yl)piperidin-1-ylcarbonyl]-1H-pyrrol-2-ylmethylidene}-6-chloro-1,3-dihydro-2H-indol-2-one.

¹HNMR (400 MHz, d₆-DMSO) δ13.46 (s, 1H), 11.02 (s, 1H), 7.79 (d, J=8.2 Hz, 1H), 7.66 (s, 1H), 7.03 (dd, J=8.2, 2.0 Hz, 1H), 6.89 (d, J=2.0 Hz, 1H), 3.56 (app br t, J=~4 Hz, 4H), 2.45 (br s, 4H), 2.37 (m, 1H), 2.26 (br m, 6H), 1.81 (br s, 2H), 1.25 (br s, 2H); LCMS m/z 469 [M+1]⁺.

Example 26

Proceeding as described in Example 2 above but substituting (3Z)-3-(3,5-dimethyl-4-carboxy-1H-pyrrol-2-ylmethylidene)-6-bromo-1,3-dihydro-2H-indol-2-one for (3Z)-3-(3,5-dimethyl-4-carboxy-1H-pyrrol-2-ylmethylidene)-5-fluoro-1,3-dihydro-2H-indol-2-one gave (3Z)-3-{[3,5-dimethyl-4-(morpholin-4-yl)piperidin-1-ylcarbonyl]-1H-pyrrol-2-ylmethylidene}-6-bromo-1,3-dihydro-2H-indol-2-one.

¹HNMR (400 MHz, CDCl₃) δ13.26 (s, 1H), 9.43 (s, 1H), 7.23 (d, J=8.2 Hz, 1H), 7.21 (s, 1H), 7.10 (dd, J=8.2, 2.0 Hz, 1H), 6.95 (d, J=1.6 Hz, 1H), 3.73 (m, 4H), 2.56 (br s, 4H), 2.37 (br m, 6H), 2.22 (br m, 4H), 1.9 (br s, 2H), 1.4 (br s, 2H); LCMS m/z 513, 515 [M+1]⁺.

Example 6

Synthesis of (3Z)-3-{[3,5-dimethyl-4-(morpholin-4-yl)azetidin-1-ylcarbonyl]-1H-pyrrol-2-ylmethylidene}-5-fluoro-1,3-dihydro-2H-indol-2-one

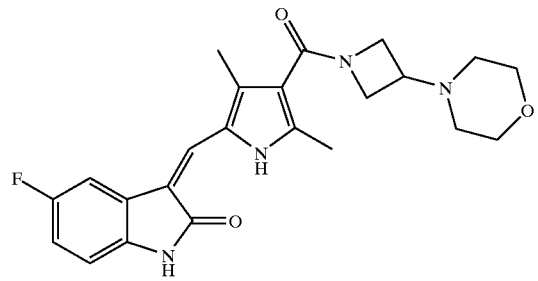

Step 1

A solution of 1-azabicyclo[1.1.0]butane, prepared from 2,3-dibromopropylamine hydrobromide (58.8 mmol) according to a known procedure described in *Tetrahedron Lett.* 40: 3761–64 (1999), was slowly added to a solution of morpholine (15.7 ml; 180 mmol) and sulfuric acid (3.3 g of 96% soln.) in anhydrous non-denaturated ethanol (250 ml) at 0° C. The reaction mixture was stirred on ice bath for 30 min., then at room temperature for 8 h. Calcium hydroxide (5.5 g) and 100 ml of water was added and the obtained slurry was stirred for 1 h and then filtered through a pad of cellite. The filtrate was concentrated and distilled at reduced pressure (20 mm Hg) to remove water and an excess of morpholine. The distillation residue was re-distilled at high vacuum using a Kugelrohr apparatus to obtain a pure 4-(azetidin-3-yl)morpholine in 33% yield (2.759 g) as a colorless oily liquid.

¹³C-NMR (CDCl₃, 100 MHz): δ66.71(2C), 59.37 (1C), 51.46 (2C), 49.95(2C) ¹H (CDCl₃, 400 MHz): δ3.727 (t, J=4.4 Hz, 4H), 3.619 (t, J=8 Hz, 2H), 3.566 (t, J=8 Hz, 2H), 3.227 (m, J=7 Hz, 1H), 2.895 (br s, 1H), 2.329 (br s, 4H)

Step 2

1-(8-Azabenztriazolyl)-ester of (3Z)-3-({3,5-dimethyl-4-carboxy]1-H-pyrrol-2-yl}methylene)-5-fluoro-1.3-dihydro-2H-indol-2-one (0.5 mmol, 210 mg) [prepared by activating (3Z)-3-(3,3-dimethyl-4-carboxy-1-H-pyrrol-2-ylmethylene)-5-fluoro-1.3-dihydro-2H-indol-2-one (480 mg; 1.6 mmol) with the HATU reagent (570 mg, 1.5 mmol) in the presence of Hunig base (3.0 mmol, 0.525 ml) in DMF (5ml) and isolated in pure form by precipitation with chloroform (5 ml) and drying on high vacuum in 92% yield (579 mg)] was suspended in anhydrous DMA (1.0 ml). A solution of 4-(azetidin-3-yl)-morpholine; (142.5 mg, 1 mmol) in anhydrous DMA (1.0 ml) was added in one portion and the obtained solution was stirred at room temperature for 20 min. The reaction mixture was evaporated at room temperature using an oil pump, the thick residue was diluted with 6 ml of a mixture of methanol plus diethyl amine (20:1; v/v), inoculated mechanically and placed into a refrigerator (+3° C.) for 8 hours. The precipitates were filtered (with a brief wash with an ice-cold methanol) and dried on high vacuum to give the desired product. 71.5% yield (152 mg of an orange solid)

LC/MS: +APCI: M+1=425; −APCI: M−1=423

$^{19}$F-NMR (d-DMSO, 376.5 MHz): δ−122.94 (m, 1F)

$^{1}$H (d-DMSO, 400 MHz): δ13.651 (s, 1H), 10.907 (s, 1H), 7.754 (dd, J=9.4 Hz, J=2.4 Hz, 1H), 7.700 (s, 1H), 6.935 (dt, J=8.2 Hz, J=2.4 Hz, 1H), 6.841 (dd, J=8.6 Hz, J=3.9 Hz; 1H), 3.963 (br s, 2H), 3.793 (br s, 2H), 3.581 (br t, J=4.3 Hz, 4H), 3.133 (m, 1H), 2.367 (s, 3H), 2.340 (s, 3H), 2.295 (br s, 4H)

Example 7

Proceeding as described in Example 6 above but substituting (3Z)-3-(3,5-dimethyl-4-carboxy-1H-pyrrol-2-ylmethylidene)-5-fluoro-1,3-dihydro-2H-indol-2-one with (3Z)-3-(3,5-dimethyl-4-carboxy-1H-pyrrol-2-ylmethylidene)-5-chloro-1,3-dihydro-2H-indol-2-one gave (3Z)-3-{[3-(morpholin-4-yl)azetidin-1-ylcarbonyl]-1H-pyrrol-2-ylmethylidene}-5-chloro-1,3-dihydro-2H-indol-2-one as an orange solid.

LC/MS: +APCI: M+1=441; −APCI: M−1=440,441

$^{1}$H (d-DMSO, 400 MHz): δ13.607 (s, 1H), 11.006 (s,1H), 7.976 (d, J=2.0 Hz, 1H), 7.756 (s, 1H), 7.136 (dd, J=8.2 Hz, J=2.0 Hz, 1H), 6.869 (d, J=8.2 Hz, 1H), 3.964 (br s, 2H), 3.793 (br s, 2H), 3.582 (br t, J=4.3 Hz, 4H), 3.134 (m,1H), 2.369 (s, 3H), 2.347 (s, 3H), 2.296 (br s, 4H)

Example 8

Proceeding as described in Example 6 above but using 4-(azetidin-3-yl)-cis-3,5-dimethylmorpholine (prepared in a procedure analogous to the preparation of 4-(azetidin-3-yl)-morpholine but using cis-3,5-dimethylmorpholine (20.7 g; 180 mmol) in place of morpholine) gave (3Z)-3-{[3,5-dimethyl-4-(2,5-dimethylmorpholin-4-yl)azetidin-1-ylcarbonyl]-1H-pyrrol-2-ylmethylidene}-5-fluoro-1,3-dihydro-2H-indol-2-one as an orange solid

LC/MS: +APCI: M+1=453; −APCI: M−1=451

$^{19}$F-NMR (d-DMSO, 376.5 MHz): δ−122.94 (m, 1F)

$^{1}$H (d-DMSO, 400 MHz): δ13.651 (s, 1H), 10.907 (s; 1H), 7.758 (dd, J=9.4 Hz, J=2.3 Hz; 1H), 7.700 (s, 1H), 6.935 (dt, J=8.6 Hz, J=2.7 Hz, 1H), 6.842 (dd, J=8.2 Hz, J=4.3 Hz, 1H), 3.961 (br s, 2H), 3.790 (br s, 2H), 3.546 (br m, 2H), 3.092 (m, 1H), 2.690 (br s; 2H), 2.364 (s, 3H), 2.338 (s, 3H), 1.492 (br m, 2H), 1.038 (br s, 6H)

Example 9

Proceeding as described in Example 6 above but substituting (3Z)-3-(3,5-dimethyl-4-carboxy-1H-pyrrol-2-ylmethylidene)-5-fluoro-1,3-dihydro-2H-indol-2-one with (3Z)-3-(3,5-dimethyl-4-carboxy-1H-pyrrol-2-ylmethylidene)-5-chloro-1,3-dihydro-2H-indol-2-one and 4-(azetidin-3-yl)morpholine with 4-(azetidin-3-yl)-cis-3,5-dimethylmorpholine gave (3Z)-3-{[3,5-dimethyl-4-(3,5-dimethylmorpholin-4-yl)azetidin-1-ylcarbonyl]-1H-pyrrol-2-ylmethylidene}-5-chloro-1,3-dihydro-2H-indol-2-one as an orange solid.

LC/MS: +APCI: M+1=469, 470; −APCI: M−1=468,469

$^{1}$H (d-DMSO, 400 MHz): δ13.606 (s, 1H), 11.008 (s, 1H), 7.979 (d, J=2.0 Hz, 1H), 7.758 (s, 1H), 7.138 (dd, J=8.2 Hz, J=2.0 Hz, 1H), 6.870 (d, J=8.2 Hz, 1H), 3.964 (br s, 2H), 3.790 (br s, 2H), 3.547 (br m, 2H), 3.095 (m, 1H), 2.691 (br s, 2H), 2.366 (s, 3H), 2.345 (s, 3H), 1.494 (br m, 2H), 1.039 (br s, 6H).

Example 10

Proceeding as described in Example 2 above, but substituting 4-(morpholin-4-yl)-piperidine with 2-(R)-pyrrolidin-1-ylmethylpyrrolidine prepared as described below provided (3Z)-3-{[3,5-dimethyl-2R-(pyrrolidin-1-ylmethyl)pyrrolidin-1-ylcarbonyl]-1H-pyrrol-2-ylmethylidene}-5-fluoro-1,3-dihydro-2H-indol-2-one.

Synthesis of 2(R)-pyrrolidin-1-ylmethylpyrrolidine
Step 1

To a solution of (+)-Carbobenzyloxy-D-proline (1.5 g, 6.0 mmol), EDC (2.3 g, 12.0 mmol) and HOBt (800 mg, 12.9 mmol) in DMF (20 ml) was added trietylamine (1.5 ml) and pyrrolidine (1.0 ml, 12.0 mmol). It was stirred for 18 h at rt. Sat. NaHCO$_3$ was added, it was extracted with CH2CL2 (three times). The organic layers were separated and dried over Na$_2$SO$_4$. The solvent was removed and the residue was purified by silica gel chromatography (EtOAc) to give 1-(R)-[N-(benzyloxycarbonyl)-prolyl]pyrrolidine as a white solid (94%).

$^{1}$H NMR (400 MHz, CDCl$_3$, all rotamers) δ1.57–1.66 (m, 1H), 1.71–2.02 (m, 5H), 2.04–2.19 (m, 2H), 3.26–3.43 (m, 3H), 3.44–3.78 (m, 3H), 4.41 (dd, J=4.5, 7.6 Hz, 0.5H), 4.52 (dd, J=3.7, 7.6 Hz, 0.5H), 4.99 (d, J=12.1 Hz, 0.5H), 5.05 (d, J=12.5 Hz, 0.5H), 5.13 (d, J=12.1 Hz, 0.5H), 5.20 (d, J=12.5 Hz, 0.5H), 7.27–7.38 (m, 5H).

Step 2

A mixture of 1-(R)-[N-(benzyloxycarbonyl)prolyl]pyrrolidine (2.7 g, 8.9 mmol) and 5% Pd—C catalyst (270 mg) in methanol (15 ml) were stirred under a hydrogen atmosphere for 20 h. The reaction mixture was filtered through celite and the solvent was removed yielding 2(R)-prolylpyrrolidine as a viscous oil (80%), which was used without further purification for the next step.

$^{1}$H NMR (400 MHz, d$_6$-DMSO) δ1.52–1.78 (m, 5H), 1.82–1.89 (m, 2H), 1.97–2.04 (m, 1H), 2.63–2.71 (m, 1H), 2.97–3.02 (m, 1H), 3.22–3.35 (m, 3H), 3.48–3.54 (m, 1H), 3.72 (dd, J=6.1, 8.0 Hz, 1H).

Step 3

2-(R)-Prolylpyrrolidine (1.2 g, 7.1 mmol) was dissolved in THF (10 ml). The reaction mixture was cooled to 0° C. and BH$_3$, 1M in THF (10 ml, 10 mmol) was dropwise at 0 C. The reaction mixture was refluxed for 16 h, 3 M HCl (4.7 ml). 2 M NaOH solution was added until pH 10 was reached. The product was extracted with 5% MeOH in CH$_2$Cl$_2$ (three times). The organic layers were dried over Na$_2$SO$_4$ and the solvent was removed to provide the title compound as a slightly yellow liquid (73%), which was used without further purification for the next step.

$^{1}$H NMR (400 MHz, d$_6$-DMSO) δ1.22–1.30 (m, 1H), 1.55–1.69 (m, 6H), 1.71–1.79 (m, 1H), 2.26–2.30 (m, 1H), 2.33–2.38 (m, 1H), 2.40–2.45 (m, 4H), 2.65–2.71 (m, 1H), 2.78–2.84 (m, 1H), 3.02–3.09 (m, 1H).

Example 11

Proceeding as described in Example 2 above, but substituting 4-(morpholin-4-yl)-piperidine with 2-(S)-pyrrolidin-1-ylmethylpyrrolidine (prepared as described above, by substituting (+)-carbobenzyloxy-D-proline with carbobenzyloxy-L-proline) provided (3Z)-3-{[3,5-dimethyl-2S-(pyrrolidin-1-ylmethyl)pyrrolidin-1-ylcarbonyl]-1H-pyrrol-2-ylmethylidene}-5-fluoro-1,3-dihydro-2H-indol-2-one.

Synthesis of Examples 20, 21, 24, 16, 17, 22 and 23

1. Synthesis side chains 4, 5 and 6.

¹H NMR (CDCl₃) δ3.25 (m, 4H), 3.40 (m, 4H), 3.47 (m, 2H), 3.61 (m, 2H), 3.70 (m, 4H), 3.77 (s, 2H).

The same reactions were carried on at the same scales and conditions except that the sequence of morpholine and piperazine-1-carboxylic acid t-butyl ester was alternated. 4-(2-Chloro-acetyl)-piperazine-1-carboxylic acid t-butyl ester 3 and the TFA salt of 2-morpholin-4-yl-1-piperazin-1-yl-ethanone 5 (4.0 g, 91%) were obtained correspondingly.

¹H NMR (CDCl₃) δ3.06 (t, J=5.4 Hz, 2H), 3.14 (t, J=5.4 Hz, 4H), 3.20 (m, 2H), 3.24 (m, 2H), 3.53 (t, J=5.2 Hz, 2H), 3.71 (t, J=5.4 Hz, 2H), 3.84 (m, 4H), 4.15 (s, 2H).

4 or 5 (5 mmol, 2.2 g) in THF (10 mL) was dropped into the suspension of a well stirred mixture of NaH (50 mmol, 1.9 g) in THF (50 mL). The resulting mixture was stirred overnight at 50° C. and then quenched with H₂O (5 mL)

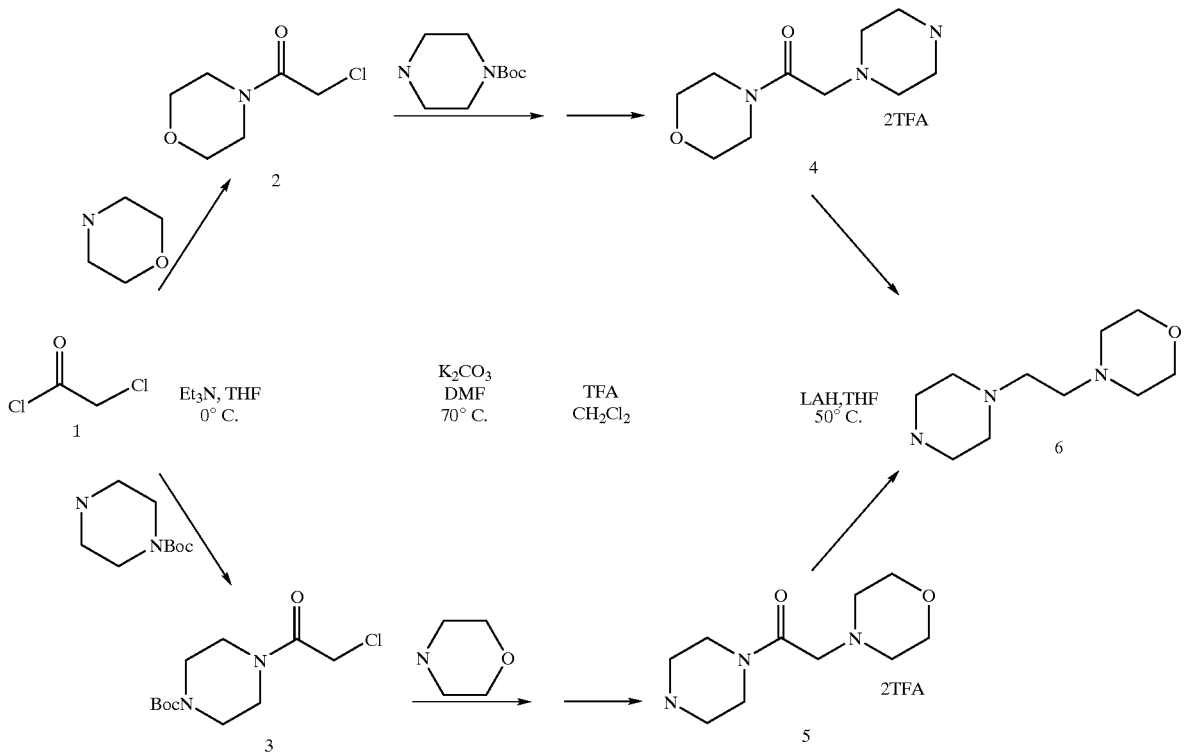

To the solution of morpholine (10 mmol, 0.872 mL) and Et₃N (15 mmol, 2.09 mL) in THF (20 mL) at 0° C. was dropped in chloroacetyl chloride 1 (12 mmol, 0.956 mL). The mixture was stirred at 0° C. for 4 h and then r.t. overnight. The reaction was quenched with H₂O and evaporated to dryness. Purification by column chromatography (CH₂Cl₂/CH₃OH=50/1) gave 2-chloro-1-morpholin-4-yl-ethanone 2 (1.62 g, 100%). 2 (1.6 g, 0.98 mmol) was treated with piperazine-1-carboxylic acid t-butyl ester (10 mmol, 1.86 g) in DMF (20 mL) at 70° C. for 12 h in the presence of K₂CO₃ (3 mmol, 4.14 g). Solvents were evaporated and the crude product was purified by flash chromatography (CH₂Cl₂/CH₃OH=30/1) to give 4-(2-morpholin-4-yl oxoethyl)-piperazine-1-carboxylic acid t-butyl ester 4, which was treated with TFA (5 mL) in CH₂Cl₂ (5 mL) at r.t. for 2 h. Evaporation of all solvents furnished the TFA salt of 1-morpholin-4-yl-2-piperazin-1-yl-ethanone 4 (4.1 g, 93%).

followed by 10% NaOH (10 mL) at 0° C. The white solid was filtered out and sonicating-washed with THF (4×20 mL). The combined liquid was evaporated to dryness and purified by column chromatography (CHCl₃/CH₃OH/NH₃.H₂O=15/1/0.1–10/1/0.1) to give 4-(2-piperazin-1-yl)-morpholine 6 (70 mg, 70%).

¹H NMR (CD₃COCD₃) δ2.35 (s, 1H), 2.42 (m, 12H), 2.74 (t, J=4.4 Hz, 4H), 3.57 (t, J=4.2 Hz, 4H). LCMS (m/z) 200 (M+1).

2. Condensation of the side chains 4, 5 and 6 with 5-(5-fluoro-2-oxo-1,2-dihydro-indol-3-ylidenemethyl)-2,4-dimethyl-1H-pyrrole-3-carboxylic acid.

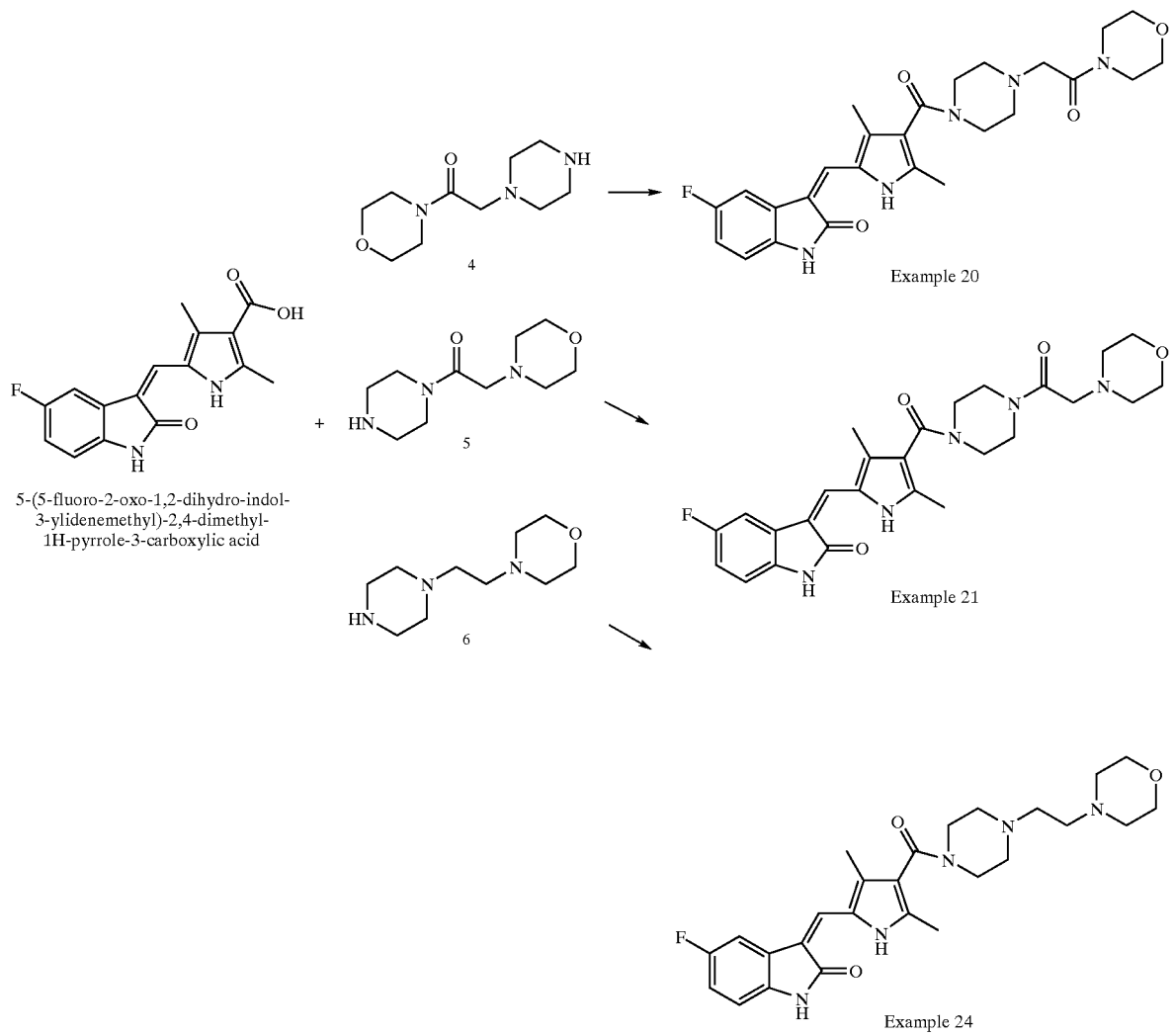

Example 20

Example 21

Example 24

To a stirred yellow muddy mixture of 5-(5-fluoro-2-oxo-1,2-dihydro-indol-3-ylidenemethyl)-2,4-dimethyl-1H-pyrrole-3-carboxylic acid (90 mg, 0.3 mmol), triethylamine (0.084 mL, 0.6 mmol), EDC (86 mg, 0.45 mmol) and HOBT (60 mg, 0.45 mmol) in DMF (0.8 mL), compound 4 (0.45 mmol) was added. The resulting solution was stirred at room temperature over night. Yellow solid product precipitated from the reaction system. The solid was isolated by vacuum filtration, washed once with ethanol (1 mL) and sonicated in diethyl ether (2 mL) for 10 min. After drying under vacuum, the compound of Example 20 (110 mg, 74% yield) was obtained as yellow solid.

$^1$H NMR (DMSO-$d_6$) δ 2.27, 2.25 (2×s, 6H, $CH_3$), 2.41 (m, 4H), 3.12 (s, 2H), 3.33 (m, 4H), 3.40 (brs, 2H), 3.52 (m, 6H, $CH_2$), 6.83(m, 1H), 6.89 (m, 1H), 7.68 (s, 1H), 7.31 (d, J=8.8 Hz, 1H) (aromatic and vinyl), 10.87 (s, 1H, CONH), 13.61 (s, 1H, NH). LC-MS (m/z) 496.0 (M+1).

The compound of Example 21 (70 mg, 47%) precipitated from the reaction mixture of compound 5 with 5-(5-fluoro-2-oxo-1,2-dihydro-indol-3-ylidenemethyl)-2,4-dimethyl-1H-pyrrole-3-carboxylic acid under the same conditions used to synthesize the compound of Example 20.

$^1$H NMR (DMSO-$d_6$) δ 2.28, 2.27 (2×s, 6H), 2.37 (m, 4H), 3.14 (s, 2H), 3.31 (m, 4H), 3.45 (brs, 2H), 3.55 (m, 6H), 6.83(m, 1H), 6.91 (m, 1H), 7.70 (s, 1H), 7.52 (dd, J=2.0, 9.2 Hz, 1H), 10.88 (s, 1H), 13.63 (s, 1H). LC-MS (m/z) 496.0 (M+1).

The compound of Example 24 (110 mg, 76%) was purified by column chromatography ($CHCl_3/CH_3OH/NH_3.H_2O$=15/1/0.1) after reaction of compound 6 with 5-(5-fluoro-2-oxo-1,2-dihydro-indol-3-ylidenemethyl)-2,4-dimethyl-1H-pyrrole-3-carboxylic acid under the same conditions used to synthesize compound of Example 20.

$^1$H NMR (DMSO-$d_6$) δ 2.27, 2.24 (2×s, 6H), 2.35 (m, 4H), 2.40 (t, J=3.8 Hz, 4H), 3.52 (t, J=4.8 Hz, 8H), 6.83(m, 1H), 6.91 (m, 1H), 7.68 (s, 1H), 7.72 (dd, J=2.4, 9.6 Hz, 1H), 10.87 (s, 1H), 13.60 (s, 1H). LC-MS (m/z) 482.2 (M+1).

3. Synthesis of side chains 9 and 10

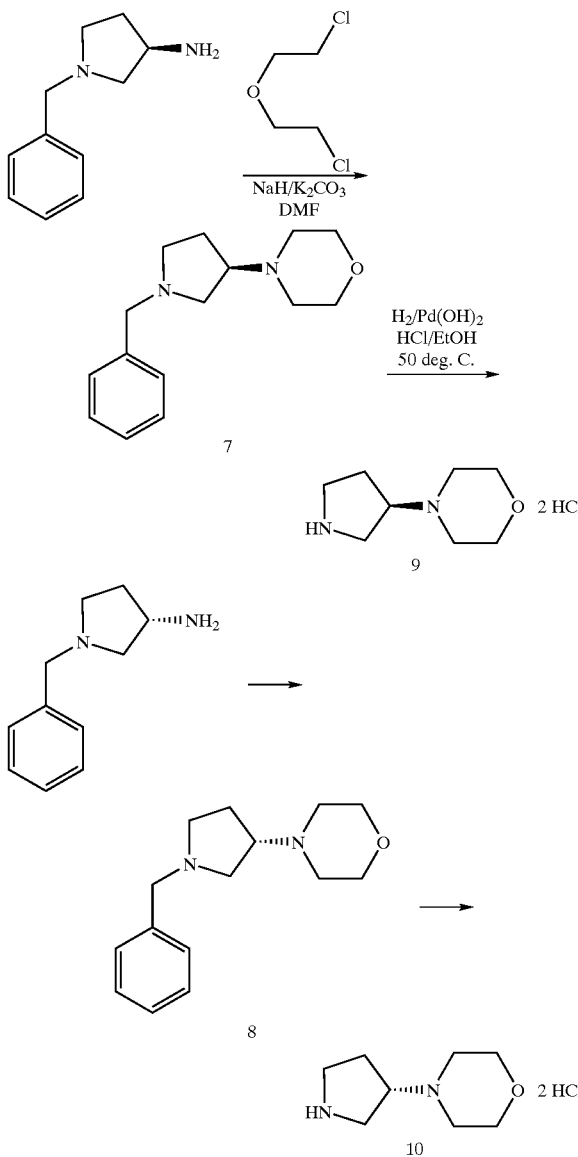

The mixture of (3R)-(−)-1-benzyl-pyrrolidin-3-ylamine (10 mmol, 1.76 g), bis(2-chloroethyl)ether (11 mmol, 1.29 mL), $K_2CO_3$ (40 mmol, 5.52 g) and NaI (0.4 mmol, 60 mg) in $CH_3CN$ (100 mL) was heated at reflux for 36 h under $N_2$. It was then absorbed on silica gel (10 g) and evaporated to dryness. The solid was loaded on silica gel column and subjected to flash chromatograph ($CH_2Cl_2/CH_3OH$=60/1–20/1). (3R)-1-(1-benzyl-pyrrolidin-3-yl)-piperidine 7 was obtained as white gum (1.4 g, 60%).

$^1$H NMR ($CDCl_3$) δ1.72 (m, 1H), 2.0 (m, 1H), 2.37 (m, 3H), 2.49 (m, 3H), 2.75 (m, 1H), 2.86 (m, 2H), 3.63, 3.61 (2×s, 2H), 3.71 (m, 4H), 7.29 (m, 5H). LC-MS (m/z) 247 (M+1).

Compound 7 (1.4 g, 6.0 mmol) was added dropwise into a flask equipped with a $H_2$ balloon and containing the mixture of $Pd(OH)_2$ (400 mg, 20% on carbon) and HCl (1.15 mL, 35% in $H_2O$, 19.5 mmol) in EtOH (50 mL). The mixture was stirred under $H_2$ at 50° C. for 10 h. Solid was filtered out and washed with hot $HOCH_3$ (2×10 mL). The combined liquid was evaporated to dryness to give HCl salt of (3R)-1-pyrrolidin-3-yl-piperidine 9 (1.4 g, 100%).

$^1$H NMR ($CD_3OD$) δ1.7 (brs, 1H), 2.42 (m, 1H), 2.57 (m, 1H), 3.31 (m, 2H), 3.42 (m, 1H), 3.65 (m, 3H), 3.73 (m, 1H), 3.93 (m, 3H), 4.06 (brs, 2H), 4.17 (m, 1H). LC-MS (m/z) 157 (M+2).

The same procedure was followed to prepare (3S)-1-(1-benzyl-pyrrolidin-3-yl)-piperidine 9 and (3S)-1-pyrrolidin-3-yl-piperidine 10 (1.5 g, 100%) from (3S)-(+)1-benzyl-pyrrolidin-3-ylamine (10 mmol, 1.76 g).

Compound 9: $^1$H NMR ($CDCl_3$) δ1.75 (m, 1H), 2.01 (m, 1H), 2.38 (m, 3H), 2.52 (m, 3H), 2.74 (m, 1H), 2.85 (m, 2H), 3.61, 3.62 (2×s, 2H), 3.71 (m, 4H), 7.30 (m, 5H). LC-MS (m/z) 247 (M+1).

Compound 10: $^1$H NMR ($CD_3OD$) δ1.72 (brs, 1H), 2.44 (m, 1H), 2.57 (m, 1H), 3.35 (m, 3H), 3.71 (m, 5H), 3.96–4.18 (m, 6H). LC-MS (m/z) 157 (M+2).

4. Synthesis of side chains 13a,b.

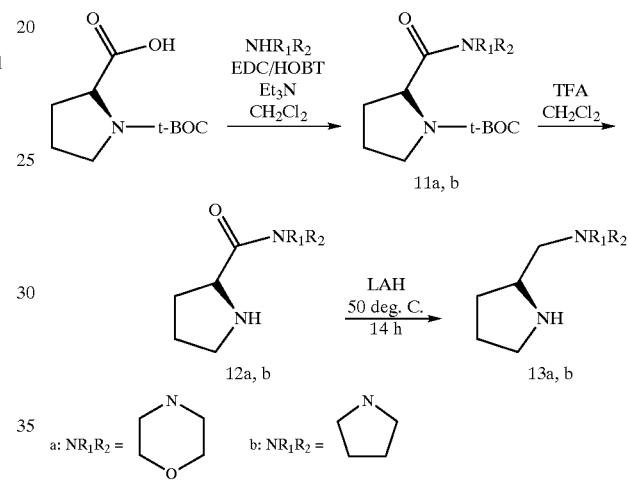

(2R)-Pyrrolidine-1,2-dicarboxylic acid 1-tert-butyl ester (2.15 g, 10 mmol) reacted with morpholine (1.3 mL, 15 mmol) in $CH_2Cl_2$ (30 mL) in the presence EDC (2.7 g, 15 mmol), HOBT (1.9 g, 15 mmol) and $Et_3N$ (2.1 mL, 15 mmol) at r.t. for 14 h. The mixture was evaporated to dryness and purified by column chromatography. After washing the resulting solid with aqueous $NaHCO_3$ followed by $H_2O$ to remove HOBT contamination, pure compound (2R)-2-(morpholine-4-carbonyl)-pyrrolidine-1-carboxylic acid tert-butyl ester 11a (1.79 g, 63%) was obtained.

Compound 11a (1.79 g, 0.63 mmol) was treated with TFA (5 mL) in $CH_2Cl_2$ (5 mL) at r.t. for 2 h. Evaporation of solvents furnished the TFA salt of (2R)-morpholin-4-yl-pyrrolidin-2-yl-methanone 12a (2.89 g, 100%), which was reduced by LAH (0.85 g, 5 eq.) in THF (50 mL) at 50° C. for 12 h. The reaction was quenched with $H_2O$ (2.4 mL) and 10% NaOH (2.4 mL). The white solid $Al_2O_3$ was filtered off and washed with THF (3×10 mL). After removing solvents from the combined liquid, clear gummy product (2R)-4-pyrrolidin-2-ylmethyl-morpholine 13a (1.1 g, 95%) was obtained.

Following the same procedure, pyrrolidine (1.06 g, 15 mmol) was used instead of morpholine to synthesize (2R)-pyrrolidin-2-ylmethyl pyrrolidine 13b.

6. Condensation of side chains 9, 10, and 13a,b with 5-(5-fluoro-2-oxo-1,2-dihydro-indol-3-ylidenemethyl)-2,4-dimethyl-1H-pyrrole-3-carboxylic acid

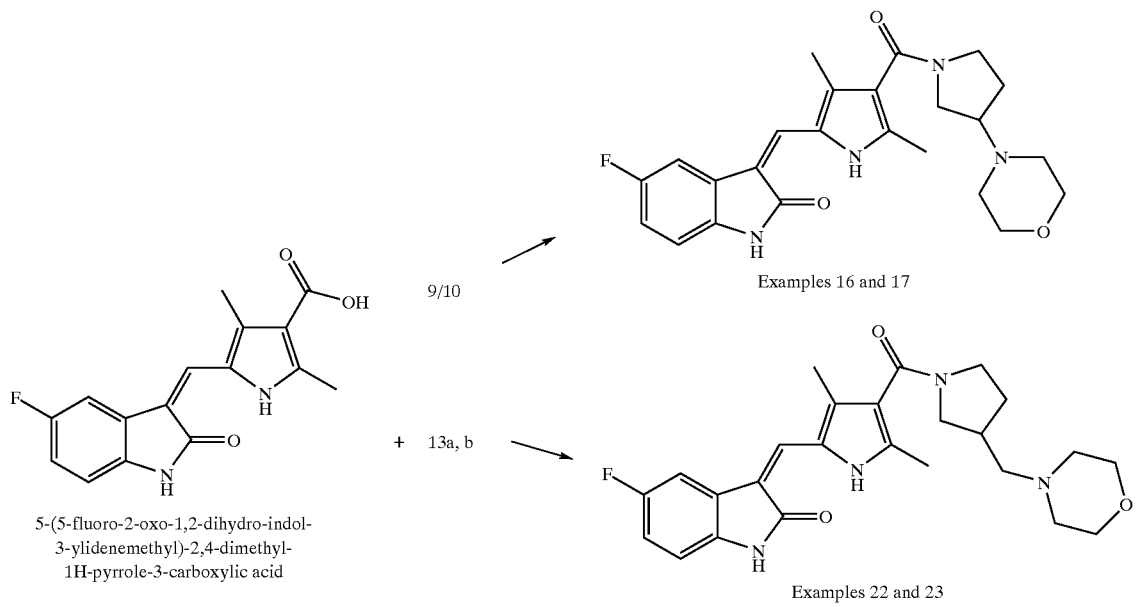

Examples 16 and 17

Examples 22 and 23

Following the previous conditions (see the synthesis of Example 21), 5-(5-fluoro-2-oxo-1,2-dihydro-indol-3-ylidenemethyl)-2,4-dimethyl-1H-pyrrole-3-carboxylic acid condensed with 9 gave the compound of Example 16 (85 mg, 65%).

$^1$H NMR (DMSO-d$_6$) δ1.67 (m, 1H), 2.0 (m, 1H), 2.06, 2.31(2×s, 6H), 2.34 (m, 3H), 2.77, 3.01, 3.22, 3.36, 3.65 (m, 6H), 3.46 (m, 2H), 3.52(m, 2H), 6.75 (m, 1H), 6.86 (m, 1H), 7.62 (s, 1H), 7.66 (d, J=9.8 Hz, 1H), 10.81 (s, 1H), 13.51 (s, 1H). LCMS (m/z) 439.0 (M+1).

The compound of Example 17 (78 mg, 60%) was made from 5-(5-fluoro-2-oxo-1,2-dihydro-indol-3-ylidenemethyl)-2,4-dimethyl-1H-pyrrole-3-carboxylic acid and 10.

$^1$H NMR (CDCl$_3$-DMSO-d$_6$) δ1.85 (m, 1H), 2.26 (m, 1H), 2.31, 2.37 (2×s, 6H), 2.52 (m, 3H), 2.8 (m, 1H), 3.18–3.94 (m, 6H), 3.68 (m, 2H), 3.73(m, 2H), 6.81 (m, 2H), 7.17 (d, J=8.4 Hz, 1H), 7.30 (s, 1H), 10.07 (s, 1H), 13.54 (s, 1H). LCMS (m/z) 439.4 (M+1).

The compound of Example 22 (80%) was made from 5-(5-fluoro-2-oxo-1,2-dihydro-indol-3-ylidenemethyl)-2,4-dimethyl-1H-pyrrole-3-carboxylic acid and 13a.

$^1$H NMR (CDCl$_3$) δ2.04 (m, 4H), 2.3 (m, 3H), 2.41, 2.28 (2×s, 6H), 2.77, 2.61 (m, 3H), 3.33 (m, 1H), 3.53 (m. 1H), 3.71 (m, 4H), 4.54 (m, 1H), 6.82 (m, 2H), 7.15 (d, J=8.4 Hz, 1H), 7.27(s, 1H), 8.51 (s, 1H), 13.33 (s, 1H). LC-MS (m/z) 453.2 (M+1).

The compound of Example 23 (77%) was made from 5-(5-fluoro-2-oxo-1,2-dihydro-indol-3-ylidenemethyl)-2,4-dimethyl-1H-pyrrole-3-carboxylic acid and 13b.

$^1$H NMR (CDCl$_3$) δ1.93, 2.04 (m, 7H), 2.41, 2.30 (2×s, 6H), 2.76, 2.62 (m, 3H), 3.33 (m, 1H), 3.53 (m. 1H), 3.71 (m, 4H), 4.55 (m, 1H), 6.82 (m, 2H), 7.17 (d, J=8.8 Hz, 1H), 7.27(m, 2H), 8.15 (s, 1H), 13.32 (s, 1H). LC-MS (m/z) 453.2 (M+1).

Biological Examples
PDGFR Bioassay

This assay is used to analyze the in vitro kinase activity of FGF1-R in an ELISA assay.

Materials and Reagents

1. Corning 96-well Elisa plates
2. 28D4C10 monoclonal anti-PDGFR antibody (SUGEN, Inc.).
3. PBS.
4. TBST Buffer.
5. Blocking Buffer (same as for EGFR bioassay).
6. PDGFR-β expressing NIH 3T3 cell lysate (SUGEN, Inc.).
7. TBS Buffer.
8. TBS+10% DMSO.
9. ATP.
10. MnCl$_2$.
11. Kinase buffer phosphorylation mix: for 10 ml, mix 250 μl 1M TRIS, 200 μl 5M NaCl, 100 μl 1M MnCl$_2$ and 50 μl 100 mM Triton X-100 in enough dH$_2$O to make 10 ml.
12. NUNC 96-well V bottom polypropylene plates.
13. EDTA.
14. Rabbit polyclonal anti-phosphotyrosine serum (SUGEN, Inc.).
15. Goat anti-rabbit IgG peroxidase conjugate (Biosource Cat. No. ALI0404).
16. ABTS.
17. Hydrogen peroxide, 30% solution.
18. ABTS/H$_2$O$_2$.
19. 0.2 M HCl.

Procedure

1. Coat Corning 96 well ELISA plates with 0.5 μg 28D4C10 in 100 μl PBS per well, store overnight at 4° C.
2. Remove unbound 28D4C10 from wells by inverting plate to remove liquid. Wash 1× with dH$_2$O. Pat the plate on a paper towel to remove excess liquid.
3. Add 150 μl of Blocking Buffer to each well. Incubate for 30 min. at room temperature with shaking.
4. Wash plate 3× with deionized water, then once with TBST. Pat plate on a paper towel to remove excess liquid and bubbles.
5. Dilute lysate in HNTG (10 μg lysate/100 μl HNTG).
6. Add 100 μl of diluted lysate to each well. Shake at room temperature for 60 min.

7. Wash plates as described in Step 4.
8. Add 80 µl working kinase buffer mix to ELISA plate containing captured PDGFR.
9. Dilute test compound 1:10 in TBS in 96-well polypropylene plates.
10. Add 10 µl diluted test compound to ELISA plate. To control wells, add 10 µl TBS+10% DMSO. Incubate with shaking for 30 minutes at room temperature.
11. Add 10 µl ATP directly to all wells except negative control well (final well volume should be approximately 100 µl with 20 µM ATP in each well.) Incubate 30 minutes with shaking.
12. Stop reaction by adding 10 µl of EDTA solution to each well.
13. Wash 4× with deionized water, twice with TBST.
14. Add 100 µl anti-phosphotyrosine (1:3000 dilution in TBST) per well. Incubate with shaking for 30–45 min. at room temperature.
15. Wash as in Step 4.
16. Add 100 µl Biosource Goat anti-rabbit IgG peroxidase conjugate (1:2000 dilution in TBST) to each well. Incubate with shaking for 30 min. at room temperature.
17. Wash as in Step 4.
18. Add 100 µl of $ABTS/H_2O_2$ solution to each well.
19. Incubate 10 to 30 minutes with shaking. Remove any bubbles.
20. If necessary stop reaction with the addition of 100 µl 0.2 M HCl per well.
21. Read assay on Dynatech MR7000 ELISA reader with test filter at 410 nM and reference filter at 630 nM.

GST-FLK-1 Bioassay

This assay analyzes the tyrosine kinase activity of GST-Flk1 on poly(glu,tyr) peptides.

Materials and Reagents

1. Corning 96-well ELISA plates (Corning Catalog No. 5805-96).
2. poly(glu,tyr) 4:1, lyophilizate (Sigma Catalog #P0275).
3. Preparation of poly(glu,tyr)(pEY) coated assay plates: Coat 2 ug/well of poly(glu,tyr)(pEY) in 100 ul PBS, hold at room temperature for 2 hours or at 4° C. overnight. Cover plates well to prevent evaporation.
4. PBS Buffer: for 1 L, mix 0.2 g $KH_2PO_4$, 1.15 g $Na_2HPO_4$, 0.2 g KCl and 8 g NaCl in approx. 900 ml $dH_2O$. When all reagents have dissolved, adjust the pH to 7.2 with HCl. Bring total volume to 1 L with dH2O.
5. PBST Buffer: to 1 L of PBS Buffer, add 1.0 ml Tween-20.
6. TBB—Blocking Buffer: for 1 L, mix 1.21 g TRIS, 8.77 g NaCl, 1 ml TWEEN-20 in approximately 900 ml $dH_2O$. Adjust pH to 7.2 with HCl. Add 10 g BSA, stir to dissolve. Bring total volume to 1 L with $dH_2O$. Filter to remove particulate matter.
7. 1% BSA in PBS: To make a 1× working solution, add 10 g BSA to approx. 990 ml PBS buffer, stir to dissolve. Adjust total volume to 1 L with PBS buffer, filter to remove particulate matter.
8. 50 mM Hepes pH 7.5.
9. GST-Flk1cd purified from sf9 recombinant baculovirus transformation (SUGEN, Inc.).
10. 4% DMSO in $dH_2O$.
11. 10 mM ATP in $dH_2O$.
12. 40 mM $MnCl_2$
13. Kinase Dilution Buffer (KDB): mix 10 ml Hepes (pH 7.5), 1 ml 5M NaCl, 40 µL 100 mM sodium orthovanadate and 0.4 ml of 5% BSA in $dH_2O$ with 88.56 ml $dH_2O$.
14. NUNC 96-well V bottom polypropylene plates, Applied Scientific Catalog #AS-72092

15. EDTA: mix 14.12 g ethylenediaminetetraacetic acid (EDTA) to approx. 70 ml $dH_2O$. Add 10 N NaOH until EDTA dissolves. Adjust pH to 8.0. Adjust total volume to 100 ml with $dH_2O$.
16. Antibody Dilution Buffer: mix 10 ml of 5% BSA in PBS buffer with 89.5 ml TBST.
17. Anti-phosphotyrosine monoclonal antibody conjugated to horseradish peroxidase (PY99 HRP, Santa Cruz Biotech).
18. 2,2'-Azinobis(3-ethylbenzthiazoline-6-sulfonic acid (ABTS, Moss, Cat. No. ABST).
19. 10% SDS.

Procedure

1. Coat Corning 96-well ELISA plates with 2 µg of polyEY peptide in sterile PBS as described in step 3 of Materials and Reagents.
2. Remove unbound liquid from wells by inverting plate. Wash once with TBST. Pat the plate on a paper towel to remove excess liquid.
3. Add 100 µl of 1% BSA in PBS to each well. Incubate, with shaking, for 1 hr. at room temperature.
4. Repeat step 2.
5. Soak wells with 50 mM HEPES (pH7.5) (150 µl/well).
6. Dilute test compound with $dH_2O$/4% DMSO to 4 times the desired final assay concentration in 96-well polypropylene plates.
7. Add 25 µl diluted test compound to ELISA plate. In control wells, place 25 µl of $dH_2O$/4% DMSO.
8. Add 25 µl of 40 mM $MnCl_2$ with 4×ATP (2 µM) to each well.
9. Add 25 µl 0.5M EDTA to negative control wells.
10. Dilute GST-Flk1 to 0.005 µg(5 ng)/well with KDB.
11. Add 50 µl of diluted enzyme to each well.
12. Incubate, with shaking, for 15 minutes at room temperature.
13. Stop reaction by adding 50 µl of 250 mM EDTA (pH 8.0).
14. Wash 3× with TBST and pat plate on paper towel to remove excess liquid.
15. Add 100 µl per well anti-phosphotyrosine HRP conjugate, 1:5,000 dilution in antibody dilution buffer. Incubate, with shaking, for 90 min. at room temperature.
16. Wash as in step 14.
17. Add 100 µl of room temperature ABTS solution to each well.
18. Incubate, with shaking, for 10 to 15 minutes. Remove any bubbles.
19. Stop reaction by adding 20 µl of 10% SDS to each well.
20. Read results on Dynatech MR7000 ELISA reader with test filter at 410 nM and reference filter at 630 nM.

C-KIT Assay

This assay is used to detect the level of c-kit tyrosine phosphorylation.

MO7E (human acute myeloid leukemia) cells were serum starved overnight in 0.1% serum. Cells were pre-treated with the compound (concurrent with serum starvation), prior to ligand stimulation. Cells were stimulated with 250 ng/ml rh-SCF for 15 minutes. Following stimulation, cells were lysed and immunoprecipitated with an anti-c-kit antibody. Phosphotyrosine and protein levels were determined by Western blotting.

HUV-EC-C Assay

This assay is used to measure a compound's activity against PDGF-R, FGF-R, VEGF, aFGF or Flk-1/KDR, all of which are naturally expressed by HUV-EC cells.

DAY 0

1. Wash and trypsinize HUV-EC-C cells (human umbilical vein endothelial cells, (American Type Culture Collection, catalogue no. 1730 CRL). Wash with Dulbecco's phosphate-buffered saline (D-PBS, obtained from Gibco BRL, catalogue no. 14190-029) 2 times at about 1 ml/10 cm² of tissue culture flask. Trypsinize with 0.05% trypsin-EDTA in non-enzymatic cell dissociation solution (Sigma Chemical Company, catalogue no. C-1544). The 0.05% trypsin is made by diluting 0.25% trypsin/1 mM EDTA (Gibco, catalogue no. 25200-049) in the cell dissociation solution. Trypsinize with about 1 ml/25–30 cm² of tissue culture flask for about 5 minutes at 37° C. After cells have detached from the flask, add an equal volume of assay medium and transfer to a 50 ml sterile centrifuge tube (Fisher Scientific, catalogue no. 05-539-6).

2. Wash the cells with about 35 ml assay medium in the 50 ml sterile centrifuge tube by adding the assay medium, centrifuge for 10 minutes at approximately 200×g, aspirate the supernatant, and resuspend with 35 ml D-PBS. Repeat the wash two more times with D-PBS, resuspend the cells in about 1 ml assay medium/15 cm² of tissue culture flask. Assay medium consists of F12K medium (Gibco BRL, catalogue no. 21127-014) and 0.5% heat-inactivated fetal bovine serum. Count the cells with a Coulter Counter® (Coulter Electronics, Inc.) and add assay medium to the cells to obtain a concentration of $0.8–1.0\times10^5$ cells/ml.

3. Add cells to 96-well flat-bottom plates at 100 $\mu$l/well or $0.8–1.0\times10^4$ cells/well, incubate ~24 h at 37° C., 5% $CO_2$.

DAY 1

1. Make up two-fold test compound titrations in separate 96-well plates, generally 50 $\mu$M on down to 0 $\mu$M. Use the same assay medium as mentioned in day 0, step 2 above. Titrations are made by adding 90 $\mu$l/well of test compound at 200 $\mu$M (4× the final well concentration) to the top well of a particular plate column. Since the stock test compound is usually 20 mM in DMSO, the 200 $\mu$M drug concentration contains 2% DMSO.

A diluent made up to 2% DMSO in assay medium (F12K+0.5% fetal bovine serum) is used as diluent for the test compound titrations in order to dilute the test compound but keep the DMSO concentration constant. Add this diluent to the remaining wells in the column at 60 $\mu$l/well. Take 60 $\mu$l from the 120 $\mu$l of 200 $\mu$M test compound dilution in the top well of the column and mix with the 60 $\mu$l in the second well of the column. Take 60 $\mu$l from this well and mix with the 60 $\mu$l in the third well of the column, and so on until two-fold titrations are completed. When the next-to-the-last well is mixed, take 60 $\mu$l of the 120 $\mu$l in this well and discard it. Leave the last well with 60 $\mu$l of DMSO/media diluent as a non-test compound-containing control. Make 9 columns of titrated test compound, enough for triplicate wells each for: (1) VEGF (obtained from Pepro Tech Inc., catalogue no. 100–200, (2) endothelial cell growth factor (ECGF) (also known as acidic fibroblast growth factor, or aFGF) (obtained from Boehringer Mannheim Biochemica, catalogue no. 1439 600), or, (3) human PDGF B/B (1276-956, Boehringer Mannheim, Germany) and assay media control. ECGF comes as a preparation with sodium heparin.

2. Transfer 50 $\mu$l/well of the test compound dilutions to the 96-well assay plates containing the $0.8–1.0\times10^4$ cells/ 100 $\mu$l/well of the HUV-EC-C cells from day 0 and incubate ~2 h at 37° C., 5% $CO_2$. p 3. In triplicate, add 50 $\mu$l/well of 80 $\mu$g/ml VEGF, 20 ng/ml ECGF, or media control to each test compound condition. As with the test compounds, the growth factor concentrations are 4× the desired final concentration. Use the assay media from day 0 step 2 to make the concentrations of growth factors. Incubate approximately 24 hours at 37° C., 5% $CO_2$. Each well will have 50 $\mu$l test compound dilution, 50 $\mu$l growth factor or media, and 100 $\mu$l cells, which calculates to 200 $\mu$l/well total. Thus the 4× concentrations of test compound and growth factors become 1× once everything has been added to the wells.

DAY 2

1. Add $^3$H-thymidine (Amersham, catalogue no. TRK-686) at 1 $\mu$Ci/well (10 $\mu$l/well of 100 $\mu$Ci/ml solution made up in RPMI media+10% heat-inactivated fetal bovine serum) and incubate ~24 h at 37° C., 5% $CO_2$. RPMI is obtained from Gibco BRL, catalogue no. 11875-051.

DAY 3

1. Freeze plates overnight at −20° C.

DAY 4

Thaw plates and harvest with a 96-well plate harvester (Tomtec Harvester 96®) onto filter mats (Wallac, catalogue no. 1205-401), read counts on a Wallac Betaplate™ liquid scintillation counter.

In Vivo Animal Models

Xengraft Animal Models

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice, (Rygaard and Povlsen, 1969, Acta Pathol. Microbial. Scand. 77:758–760), many different human tumor cell lines (e.g., mammary, lung, genitourinary, gastro-intestinal, head and neck, glioblastoma, bone, and malignant melanomas) have been transplanted and successfully grown in nude mice. The following assays may be used to determine the level of activity, specificity and effect of the different compounds of the present invention. Three general types of assays are useful for evaluating compounds: cellular/catalytic, cellular/biological and in vivo. The object of the cellular/catalytic assays is to determine the effect of a compound on the ability of a TK to phosphorylate tyrosines on a known substrate in a cell. The object of the cellular/biological assays is to determine the effect of a compound on the biological response stimulated by a TK in a cell. The object of the in vivo assays is to determine the effect of a compound in an animal model of a particular disorder such as cancer.

Suitable cell lines for subcutaneous xenograft experiments include C6 cells (glioma, ATCC # CCL 107), A375 cells (melanoma, ATCC # CRL 1619), A431 cells (epidermoid carcinoma, ATCC # CRL 1555), Calu 6 cells (lung, ATCC # HTB 56), PC3 cells (prostate, ATCC # CRL 1435), SKOV3TP5 cells and NIH 3T3 fibroblasts genetically engineered to overexpress EGFR, PDGFR, IGF-1R or any other test kinase. The following protocol can be used to perform xenograft experiments:

Female athymic mice (BALB/c, nu/nu) are obtained from Charles River Laboratories Inc., (Wilmington, Mass.). All animals are maintained under clean-room conditions in Micro-isolator cages with Alpha-dri bedding. They receive sterile rodent chow and water ad libitum.

Cell lines are grown in appropriate medium (for example, MEM, DMEM, Ham's F10, or Ham's F12 plus 5%–10% fetal bovine serum (FBS) and 2 mM glutamine (GLN)). All cell culture media, glutamine, and fetal bovine serum are purchased from Gibco Life Technologies (Grand Island, N.Y.) unless otherwise specified. All cells are grown in a humid atmosphere of 90–95% air and 5–10% $CO_2$ at 37° C. All cell lines are routinely subcultured twice a week and are negative for mycoplasma as determined by the Mycotect method (Gibco).

Cells are harvested at or near confluency with 0.05% Trypsin-EDTA and pelleted at 450×g for 10 min. Pellets are resuspended in sterile PBS or media (without FBS) to a particular concentration and the cells are implanted into the hindflank of the mice (8–10 mice per group, 2–10×10$^6$ cells/animal). Tumor growth is measured over 3 to 6 weeks using venier calipers. Tumor volumes are calculated as a product of length×width×height unless otherwise indicated. P values are calculated using the Students t-test. Test compounds in 50–100 µL excipient (DMSO, or VPD:D5W) can be delivered by IP injection at different concentrations generally starting at day one after implantation.

Tumor Invasion Model

The following tumor invasion model has been developed and may be used for the evaluation of therapeutic value and efficacy of the compounds identified to selectively inhibit KDR/FLK-1 receptor.

Procedure 8 week old nude mice (female) (Simonsen Inc.) are used as experimental animals. Implantation of tumor cells can be performed in a laminar flow hood. For anesthesia, Xylazine/Ketamine Cocktail (100 mg/kg ketamine and 5 mg/kg Xylazine) are administered intraperitoneally. A midline incision is done to expose the abdominal cavity (approximately 1.5 cm in length) to inject 10$^7$ tumor cells in a volume of 100 µl medium. The cells are injected either into the duodenal lobe of the pancreas or under the serosa of the colon. The peritoneum and muscles are closed with a 6-0 silk continuous suture and the skin is closed by using wound clips. Animals are observed daily.

Analysis

After 2–6 weeks, depending on gross observations of the animals, the mice are sacrificed, and the local tumor metastases to various organs (lung, liver, brain, stomach, spleen, heart, muscle) are excised and analyzed (measurement of tumor size, grade of invasion, immunochemistry, in situ hybridization determination, etc.).

Apoptosis Assay

MO7E cells are incubated +/−SCF and +/−compound in 10% FBS with rh-GM-CSF(10 ng/mL) and rh-IL-3 (10 ng/mL). Samples are assayed at 24 and 48 hours. To measure activated caspase-3, samples are washed with PBS and permeabilized with ice-cold 70% ethanol. The cells are then stained with PE-conjugated polyclonal rabbit anti-active caspase-3 and analyzed by FACS. To measure cleaved PARP, samples are lysed and analyzed by western blotting with an anti-PARP antibody.

Measurement of Cell Toxicity

Therapeutic compounds should be more potent in inhibiting receptor tyrosine kinase activity than in exerting a cytotoxic effect. A measure of the effectiveness and cell toxicity of a compound can be obtained by determining the therapeutic index, i.e., IC$_{50}$/LD$_{50}$. IC$_{50}$, the dose required to achieve 50% inhibition, can be measured using standard techniques such as those described herein. LD$_{50}$, the dosage which results in 50% toxicity, can also be measured by standard techniques as well (Mossman, 1983, *J. Immunol. Methods*, 65:55–63), by measuring the amount of LDH released (Korzeniewski and Callewaert, 1983, *J. Immunol. Methods*, 64:313, Decker and Lohmann-Matthes, 1988, *J. Immunol. Methods*, 115:61), or by measuring the lethal dose in animal models. Compounds with a large therapeutic index are preferred. The therapeutic index should be greater than 2, preferably at least 10, more preferably at least 50.

The activity of compounds of the present invention against other kinases can be determined using assays and methods that are well known in the art. Some such assays are described in WO 01/60814 the disclosure of which is incorporated herein by reference in its entirety. The assays include, but are not limited to, a bio-flk-1 assay, an EGF receptor-HER2 chimeric receptor assay in whole cells, a bio-src assay, a bio-lck assay and an assay measuring the posphorylation function of raf The protocols for these assays are found in U.S. Pat. No. 6,130,238, which is incorporated by reference in its entirety herein.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent patent application or publication were so individually denoted.

What is claimed is:

1. A compound of Formula (IV):

(IV)

wherein:

R is:
(a) hydrogen;
(b) —PO(OR$^5$)$_2$ where each R$^5$ is independently hydrogen or alkyl;
(c) —COR$^6$ where R$^6$ is alkyl; or
(d) —CHR$^7$NR$^8$R$^9$ where R$^7$ is hydrogen or alkyl, and R$^8$ and R$^9$ are independently hydrogen or alkyl; or R$^8$ and R$^9$ together with the nitrogen atom to which they are attached form a heterocycloamino ring;

R$^1$ is hydrogen, alkyl, alkoxy, hydroxy, trifluoromethyl, trifluoromethoxy, F, Cl, Br, or I;

R$^2$ is hydrogen, alkyl, heteroaryl, alkoxy, hydroxy, F, Cl, Br, or I;

R$^3$ is hydrogen or alkyl;

R$^4$ is hydrogen or alkyl;

ring A is optionally substituted heterocycloamino;

Het is cycloalkylaminoalkyl, cycloalkylalkylaminoalkyl, heteroaryl, heterocycle, heterocyclylcarbonylalkyl, heterocyclylalkylcarbonyl, or heterocyclylalkyl;

X is NR$_8$R$_9$ or OR$_8$; and n is 0 or 1; or a pharmaceutically acceptable salt thereof.

2. A compound of Formula (I):

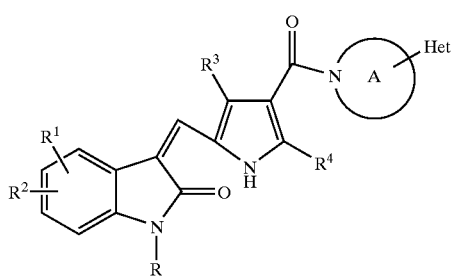

wherein:
R is:
(a) hydrogen;
(b) —PO(OR⁵)₂ where each $R^5$ is independently hydrogen or alkyl;
(c) —COR⁶ where $R^6$ is alkyl; or
(d) —CHR⁷NR⁸R⁹ where $R^7$ is hydrogen or alkyl, and $R^8$ and $R^9$ are independently hydrogen or alkyl; or $R^8$ and $R^9$ together with the nitrogen atom to which they are attached form a heterocycloamino ring;
$R^1$ is hydrogen, alkyl, alkoxy, hydroxy, trifluoromethyl, trifluoromethoxy, F, Cl, Br, or I;
$R^2$ is hydrogen, alkyl, heteroaryl, alkoxy, hydroxy, F, Cl, Br, or I;
$R^3$ is hydrogen or alkyl;
$R^4$ is hydrogen or alkyl;
ring A is optionally substituted heterocycloamino;
Het is cycloalkylaminoalkyl, cycloalkylalkylaminoalkyl, heteroaryl, heterocycle, or heterocyclylalkyl; or
a pharmaceutically acceptable salt thereof.

3. The compound of one of claim 1 or 2, wherein:
$R^1$ is hydrogen, methyl, methoxy, hydroxy, F, Cl or Br; and
$R^2$ is hydrogen, methyl, methoxy, hydroxy, F, Cl or Br.

4. The compound of one of claim 1 or 2 wherein:
$R^1$ is F; and
$R^2$ is hydrogen.

5. The compound of claim 4, wherein:
$R^1$ is at the 5-position of the indolinone ring; and
R is hydrogen, —PO(OH)₂, —COCH₃, or pyrrolidin-1-ylmethyl.

6. The compound of claim 5, wherein:
R is hydrogen;
$R^3$ and $R^4$ are independently hydrogen or methyl.

7. The compound of claim 6, wherein:
$R^3$ and $R^4$ are methyl.

8. The compound of one of claim 1 or 2, wherein A is a heterocycloamino group of 4 to 6 ring atoms.

9. The compound of one of claim 1 or 2, wherein A is azetidin-1-yl, pyrrolidin-1-yl, piperidin-1-yl, or piperazin-1-yl.

10. The compound of one of claim 1 or 2, wherein Het is a heterocycle containing 4 to 6 ring atoms wherein one or two ring atoms are selected from the group consisting of nitrogen, oxygen, or sulfur, the remaining ring atoms being carbon.

11. The compound of one of claim 1 or 2, wherein Het is piperdin-1-yl, morpholin-4-yl, thiomorpholin-4-yl, piperazin-1-yl, 2,6-dimethylmorpholin-4-yl, or 2,6-dimethylpiperazin-1-yl and is located at the 3 or 4-position of the A ring.

12. The compound of claim 11, wherein A is azetidin-1-yl, pyrrolidin-1-yl, piperidin-1-yl, or piperazin-1-yl.

13. The compound of one of claim 1 or 2, wherein Het is a heterocyclylalkyl wherein the heterocyclyl ring contains 5 or 6 ring atoms wherein one or two ring atoms are selected from the group consisting of nitrogen, oxygen, or sulfur, the remaining ring atoms being carbon.

14. The compound of claim 13, wherein the Het is pyrrolidin-1-ylmethyl.

15. The compound of claim 14, wherein A is azetidin-1-yl, pyrrolidin-1-yl, piperidin-1-yl, or piperazin-1-yl.

16. The compound of claim 14, wherein A is pyrrolidin-1-yl and pyrrolidin-1-ylmethyl is at the C2-position of the pyrrolidin-1-yl ring and the stereochemistry at the C2-position of the pyrrolidin-1-yl ring is either R or S.

17. A compound selected from the group consisting of:

1                 434.5

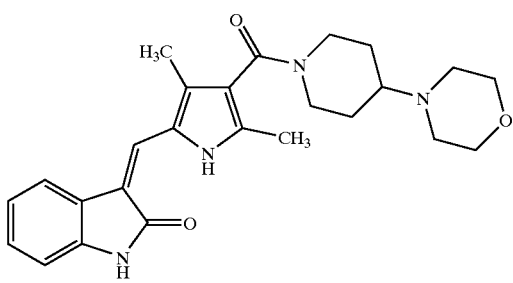

-continued
| | | |
|---|---|---|
| 2 | 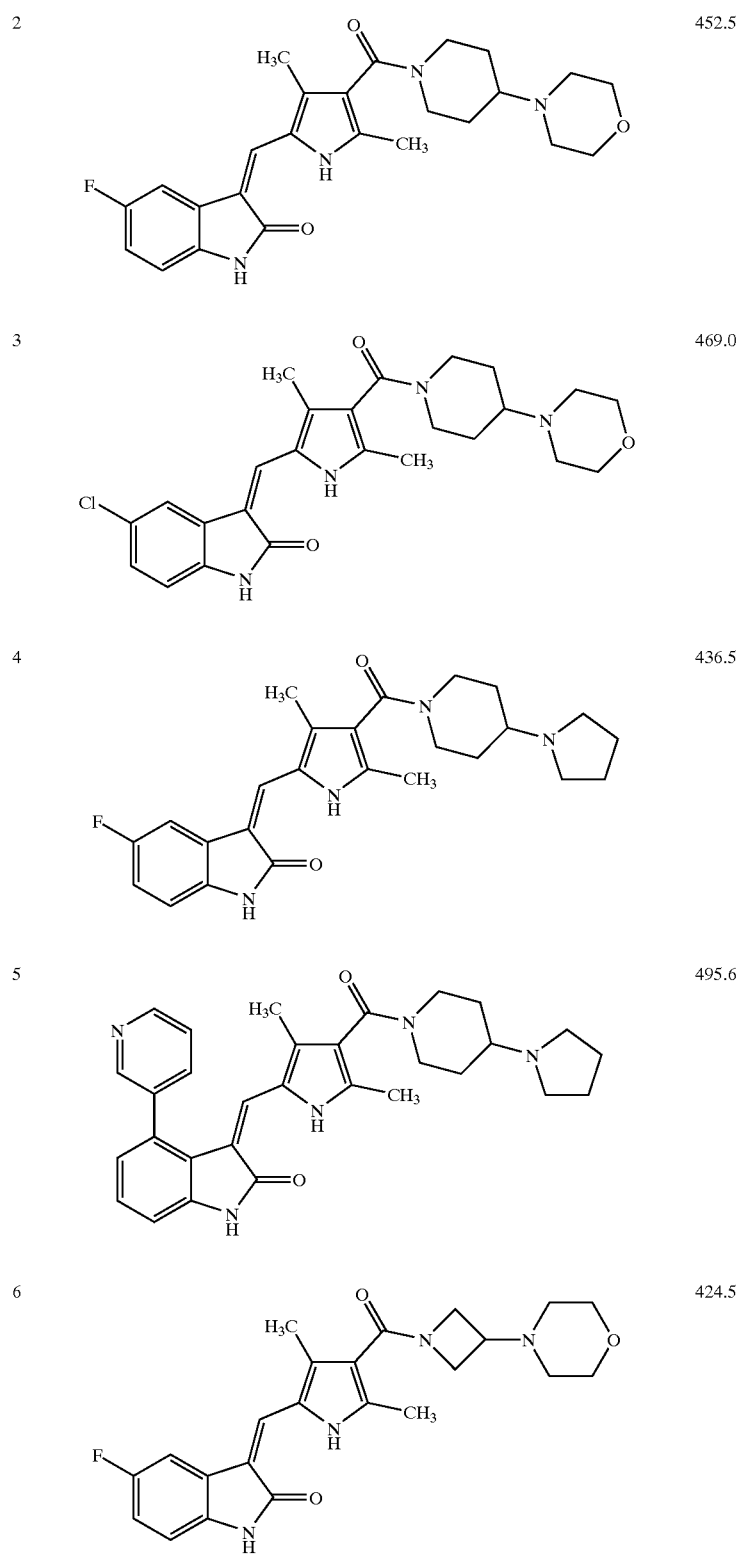 | 452.5 |
| 3 | | 469.0 |
| 4 | | 436.5 |
| 5 | | 495.6 |
| 6 | | 424.5 |

-continued
| | | |
|---|---|---|
| 7 | 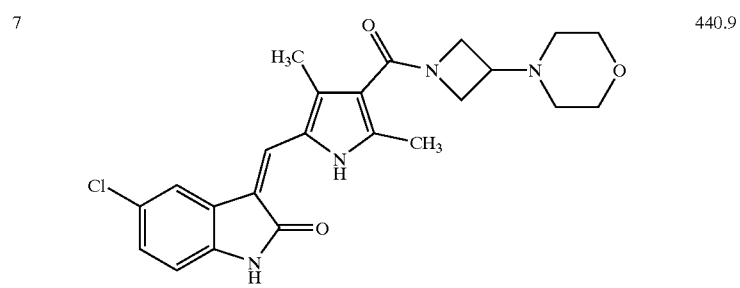 | 440.9 |
| 8 | 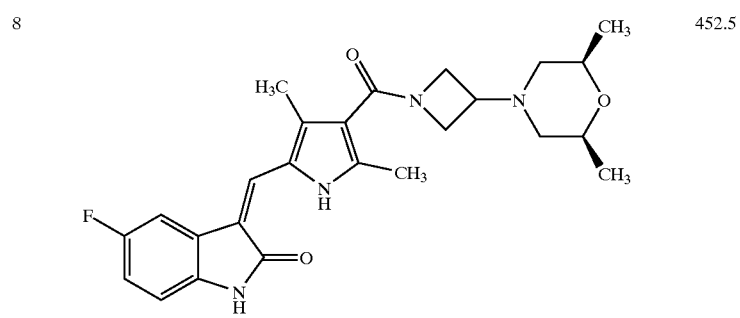 | 452.5 |
| 9 | 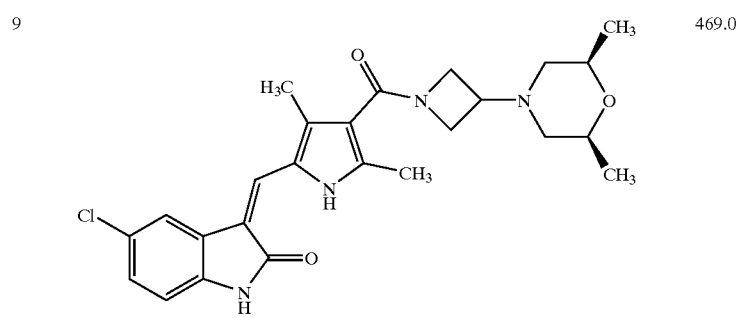 | 469.0 |
| 10 | 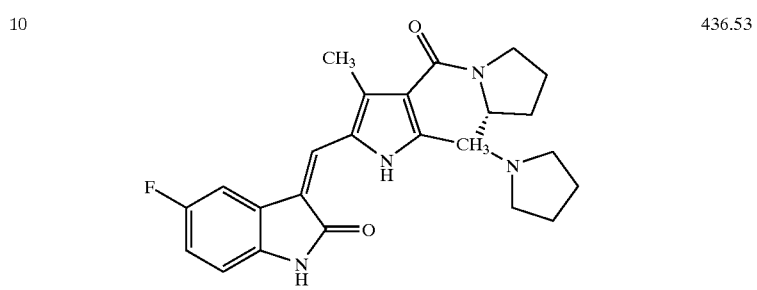 | 436.53 |
| 11 | 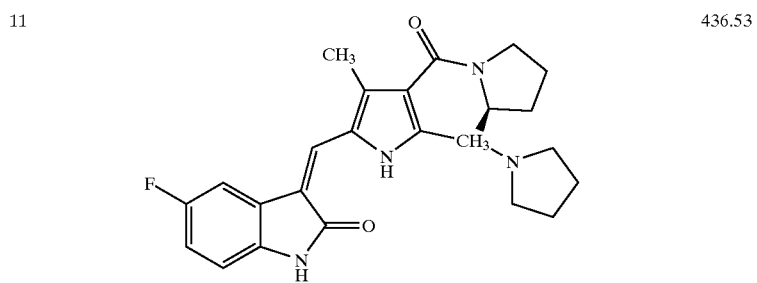 | 436.53 |

-continued
12 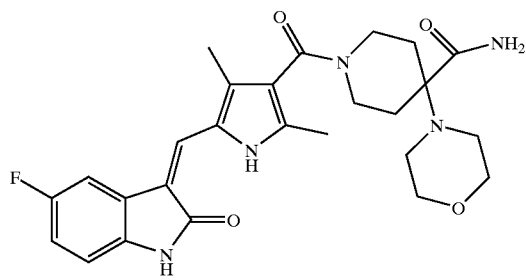
13 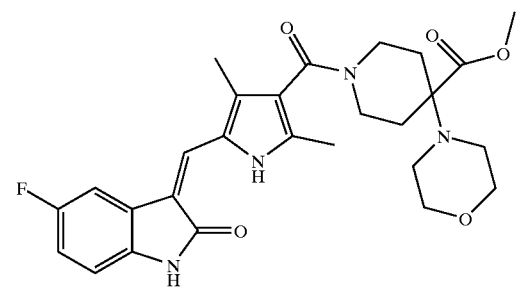
14 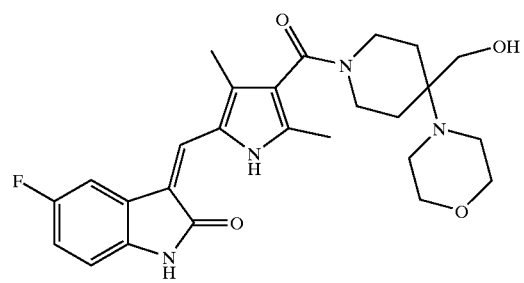
15 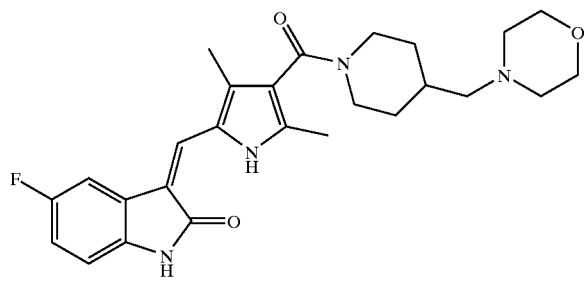
16 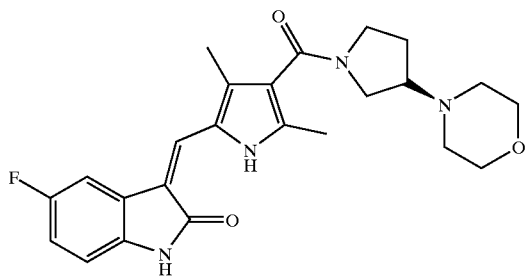

-continued
17 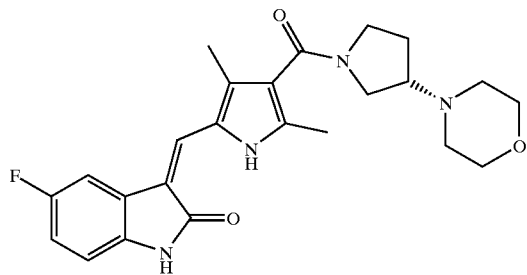
18 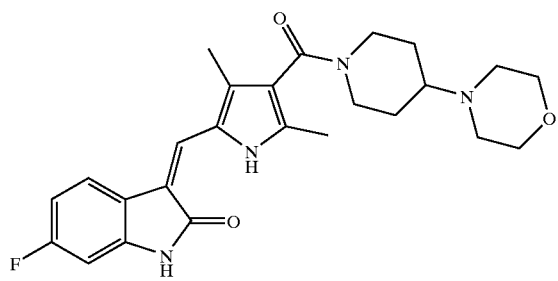
19 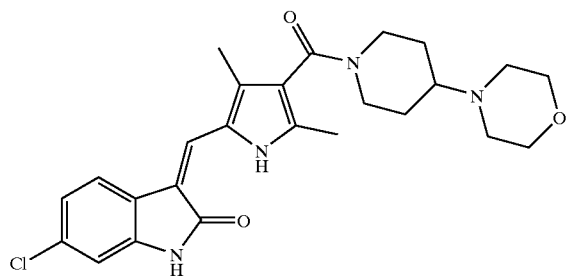
20 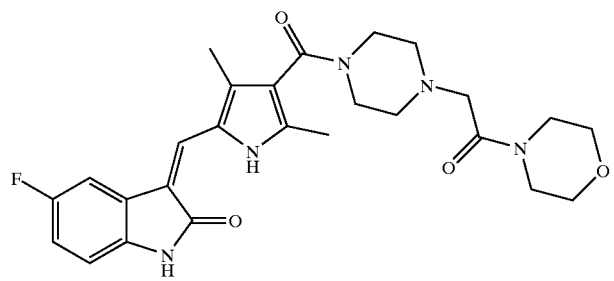
21 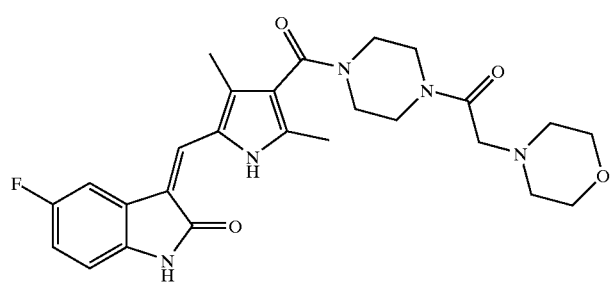

-continued

22

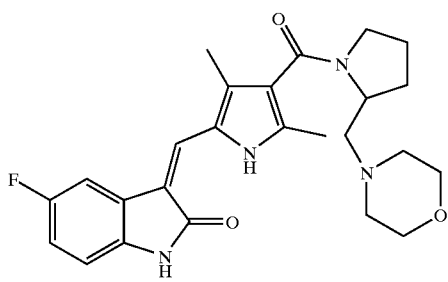

23

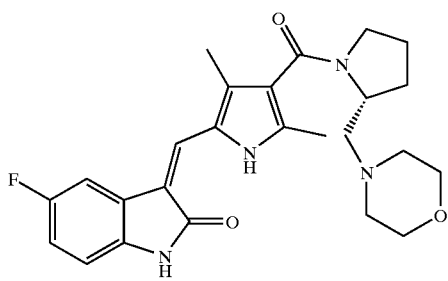

24

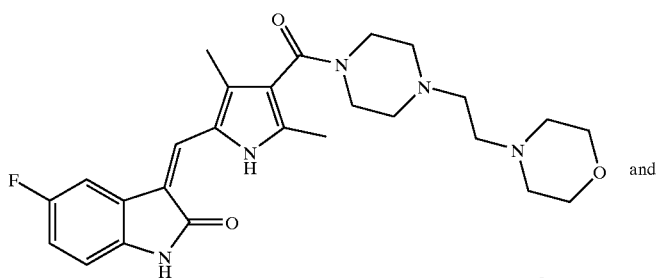

and

25

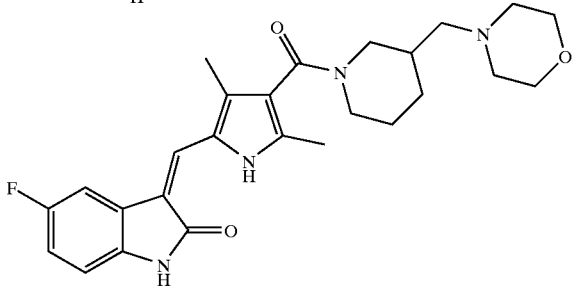

18. The compound of claim 17 wherein the compound is:

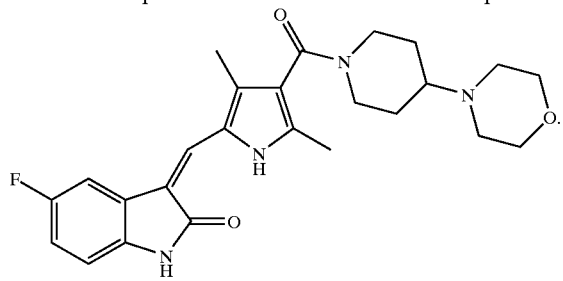

19. A pharmaceutical composition, comprising a compound or salt of one of claim 1, 2, 17, or 18 and a pharmaceutically acceptable carrier or excipient.

20. A method for the modulation of the catalytic activity of a protein kinase comprising contacting said protein kinase with a compound or salt of one of claim 1, 2, 17, or 18.

21. The method of claim 20, wherein said protein kinase is VEGFR, c-kit, and PDGFR.

22. A method for treating a protein kinase related disorder in a patient in need of such treatment comprising administering a therapeutically effective amount of a pharmaceutical composition comprising a compound or salt of any one of claim 1, 2, 17, or 18 and a pharmaceutically acceptable carrier or excipient to said patient.

23. The method of claim 22, wherein the disorder is mediated by VEGFR, c-kit, and/or PDGFR kinase.

24. The method of claim 23, wherein said protein kinase related disorder is a cancer selected from the group consisting of glioblastoma, non small-cell lung cancer, melanoma, acute myeloid leukemia and colorectal cancer.

25. The compound of any one of claim 1 or 2, where R is H.

* * * * *